United States Patent [19]

Breece et al.

[11] Patent Number: 5,759,807
[45] Date of Patent: Jun. 2, 1998

[54] PROCESS FOR PRODUCING RELAXIN

[75] Inventors: Tim Breece, San Francisco; Kirk Hayenga, San Mateo; Ernst Rinderknecht, San Carlos; Richard Vandlen, Hillsborough; Daniel Yansura, Pacifica, all of Calif.

[73] Assignee: Genentech, Inc., South San Francisco, Calif.

[21] Appl. No.: 443,568

[22] Filed: May 22, 1995

Related U.S. Application Data

[63] Continuation of Ser. No. 80,354, Jun. 21, 1993, abandoned.

[51] Int. Cl.$^6$ ............................ C12N 15/12; C12N 15/63; C12N 5/10; C07K 14/64
[52] U.S. Cl. ...................... 435/69.1; 435/69.7; 435/243; 435/320.1; 435/325; 530/300; 530/324; 536/23.1; 536/23.4
[58] Field of Search ........................ 536/23.5, 23.1, 536/23.4; 435/69.4, 68.1, 320.1, 240.2, 252.33, 69.1, 69.7, 243, 325; 530/300, 324, 350, 397

[56] References Cited

U.S. PATENT DOCUMENTS

| | | | |
|---|---|---|---|
| 4,518,526 | 5/1985 | Olson | 530/351 |
| 4,656,249 | 4/1987 | Tregear et al. | 530/324 |
| 4,758,516 | 7/1988 | Hudson et al. | 435/253 |
| 4,871,670 | 10/1989 | Hudson et al. | 435/172.3 |
| 5,023,321 | 6/1991 | Hudson et al. | 530/324 |
| 5,145,962 | 9/1992 | Hudson et al. | 530/324 |
| 5,166,191 | 11/1992 | Cronin et al. | 514/12 |
| 5,179,195 | 1/1993 | Hudson et al. | 530/324 |

FOREIGN PATENT DOCUMENTS

| | | |
|---|---|---|
| 15413/83 | 12/1983 | Australia . |
| 068 375 | 1/1983 | European Pat. Off. . |
| 101309 | 2/1984 | European Pat. Off. . |
| 112149 | 6/1984 | European Pat. Off. . |
| 518 587 | 12/1992 | European Pat. Off. . |

OTHER PUBLICATIONS

Lehninger, A.L. Biochemistry, 2nd edition, Worth Publishers, Inc., 1978, pp. 128–131.
Chang et al. Biochem. Biophy. Res. Comm 171(2):818–826 (1992).
Dimarchi et al. Intl. J. Pept. Prot. Res. 19:88–93 (1982).
Stults et al. Biomed Environ Mass. Spectrum 19:655–664, 1990.
Intl. Union of Biochemistry, Enzyme Nomenclature, 1984.
Lehninger, A.L., Biochemistry, 2nd Ed., 1975, p. 560.
Hudson, P. et al. "Structure of a genomic clone encoding biologically active human relaxin". Nature 301:628 (1983).
Hudson, P. et al. "Molecular cloning and characterization of cDNA sequences coding for rat relaxin". Nature 291:127 (1981).

Hudson, P. et al. "Relaxin gene expression in human ovaries and the predicted structure of a human preprorelaxin by anlysis of cDNA clones". The EMBO Journal 3:2333 (1984).
Haley J. et al. "Porcine Relaxin: Molecular Cloning and cDNA Structure". DNA 1:155 91982).AR.
Marriot, D. et al. "Prohormone Convertase–1 Will Process Prorelaxin a Member of the Insulin Family of Hormones". Molecular Endocrinology 9:1441 (1992).
Wright, et al. "Effect of Relaxin on Mammary Growth in the Hypophysectomized Rat". Department of Dairy Science and Animal Science, Research Center. University of Missouri–Columbia, pp. 341–353.
Gold, D. et al. "Purification of Biosynthetic Hyman Relzxin A–Chain and B–chain and Scaleup of the Chain Combination Reaction". Abst. Am.Chem. Soc. Natl. Meeting. Apr. 5–10 1992, No. BTEC–55.
Sherwood, D.O.. Relaxin, In The Physiology of Reproduction Chapter 16, pp. 585–673 (1988).
Reddy, G.K. et al.. "Purification and Chacterization Recmobinant Porcin Prorelaxin Expressed in Escherichia coli". Archives of Biochemistry and Biophysics 294:579 (1992).
Chang, E.S. et al., Biochem. Biophy. Res. Comm. 171(2):818–826 (1992).
Dimarchi, R.D. et al., Intl. J. Pept. Prot. Res. 19:88–93 (1982).
Stults, J.T. et al., Biomed. Environ. Mass. Spectrom. 19:655–664 (1990).
Intl. Union of Biochemistry, Enzyme Nomenclature (1984).
Lehninger, A.L., Biochemistry 2nd edition, 1975, p. 560.
Wetzel, R. et al. "Expression in Escherichia coli of a chemically synthesized gene for a mini–C analog of human proinsulin". Gene 16:63–71 (1981).
Castellanos, L. et al. "Expression of IL–2/proinsulin fusion protein: folding of the fusion protein and conversion into insulin by a one step removal of c–peptide and leader sequence". Protein Engineering 6(SUPP), 1993.
Derwent Publications Ltd, London, GB:class B04, AN 88–311967 and JP.A.63 230.089 (Tadeda) Sep. 26, 1988 and Patent Abstracts of Japan, vol. 13, No. 24 (C–561) (3372) Jan. 19, 1989.
Fujimoto, K. et al. "Expression and secretion of human epidermal growth factor by Escherichia coli using enterotoxin signal sequences". Journal of Biotechnology 8:77–86 (1988).

Primary Examiner—John Ulm
Assistant Examiner—Christine Saoud
Attorney, Agent, or Firm—Pennie & Edmonds LLP

[57] ABSTRACT

A process for the prokaryotic production of relaxin from non-naturally occurring forms of prorelaxin is provided. Also provided are non-naturally occurring forms of prorelaxin.

37 Claims, 26 Drawing Sheets

MKKNIAFLLKR
(SEQ. ID NO:1)         STII LEADER SEQUENCE

DSWMEEVIKLCGRELVRAQIAICGMSTWS
(SEQ. ID NO:2)         B - CHAIN

KRKPTGYGSRKKR
(SEQ. ID NO:3)         MINI C PEPTIDE

QLYSALANKCCHVGCT

FIG. 2A

| PLASMID NAME | LEADER SEQUENCE | C CHAIN SEQUENCE | CLEAVING ENZYMES |
|---|---|---|---|
| pRB250CTsc | MKKNIAFLLKR | KRKPTGYGSRKKR (SEQ ID NO:5) | TRYPSIN AND CARBOXY-PEPTIDASE C (CPB) |
| pRELCIII | MKKNIAFLLKR | DKKRTGYGSRRRK (SEQ ID NO:6) | AspN AND LysC |
| pRELCAspN | MKKNIAFLLKR | DKKRTGYGSRKKR (SEQ ID NO:7) | AspN AND TRYPSIN OR ArgC |
| PRELCLysC | MKKNIAFLLKR | KRKPTGYGSRRRK (SEQ ID NO:8) | LysC AND CPB |

FIG. 2B

| STII | B - CHAIN | MINI - C | A - CHAIN |
|---|---|---|---|

↑ 1    ↑ 2    ↑ 3

| CONST | STII/B - CHAIN | BC/MC | MC/AC |
|---|---|---|---|
| | ↓ 1 | ↓ 2 | ↓ 3 |
| pRB250CTsc | KR DS | ...WS KRKP...RKKR QL | |

| SITE | ENZYMES |
|---|---|
| 1 | TRYP.;ASP-N |
| 2 | TRYP.;ARG-C; LYS-C;ALL WITH CPB |
| 3 | TRYP.;ARG-C |

MOST FAVORABLE COMBINATIONS

ARG-C/CPB
TRYPSIN/CPB

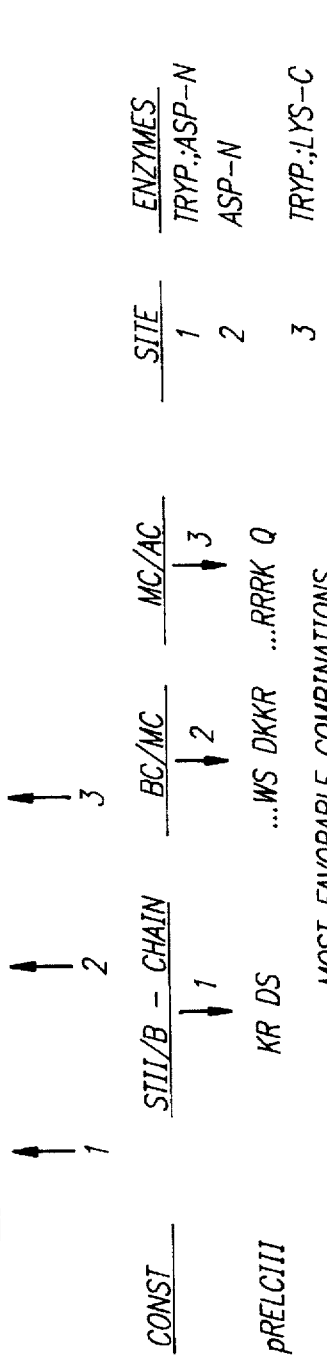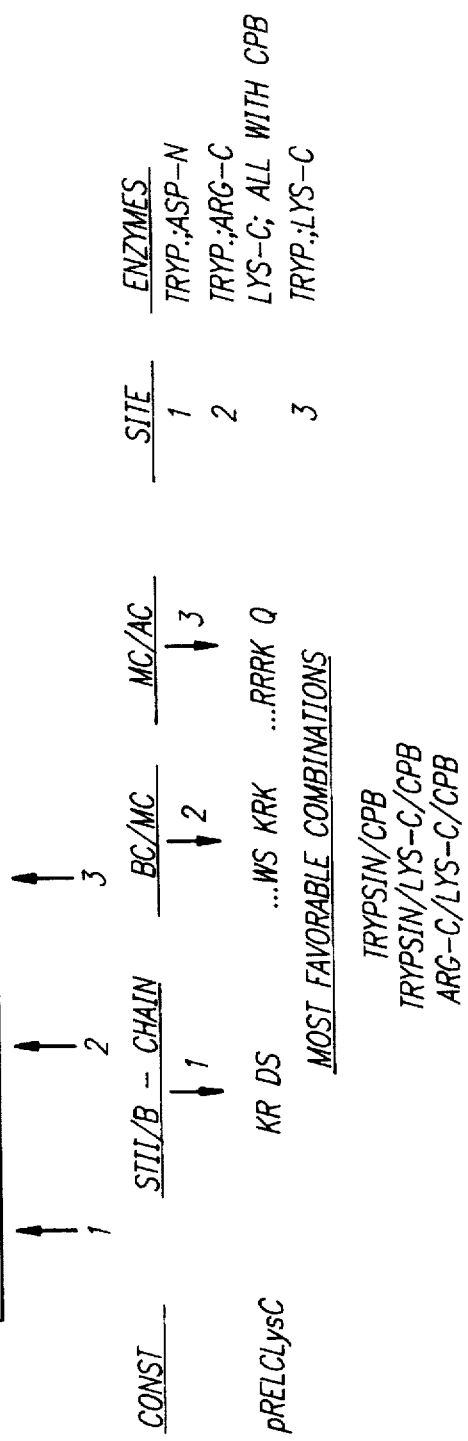

FIG. 3

```
ATG AAA AAG AAT ATC GCA TTT CTT CTT AAA CGG GAC TCA      36
Met Lys Lys Asn Ile Ala Phe Leu Leu Lys Arg Asp Ser
 1               5                  10
   STII leader   + KR TGG ATG GAG GAA GTT ATT AAA TTA TGC GGC CGC GAA TTA      75
Trp Met Glu Glu Val Ile Lys Leu Cys Gly Arg Glu Leu
         15                  20                  25
   B-chain relaxin GTT CGC GCG CAG ATT GCC ATT TGC GGC ATG AGC ACC TGG     114
Val Arg Ala Gln Ile Ala Ile Cys Gly Met Ser Thr Trp
             30                  35

AGC     AAA AGG AAA CCC ACT GGT TAT GGT TCT CGA AAA AAG  153
Ser     Lys Arg Lys Pro Thr Gly Tyr Gly Ser Arg Lys Lys
            40                  45                  50
        synthetic DNA Encoding C-Peptide AGA     CAA CTC TAC AGT GCA TTG GCT AAT AAA TGT TGC CAT  192
Arg     Gln Leu Tyr Ser Ala Leu Ala Asn Lys Cys Cys His
                        55                  60
        A-chain relaxin GTT GGT TGT ACC AAA AGA TCT CTT GCT AGA TTT TGC         228
Val Gly Cys Thr Lys Arg Ser Leu Ala Arg Phe Cys
 65              70                  75  76
```

FIG. 9B

GlyArgGluLeuValArgAlaGlnIleAlaIleCysGlyMetSerThrTrpSerLysArgSerLeuSerGlnGluAsp
GCGGCCGCGAATTAGTTCGCGCGCAGATTGCCATTTGCGGCATGAGCACCTGGAGCAAAAGGTCTCTGAGCCAGGAAGAT

AlaProGlnThrProArgProValAlaGluIleValProSerPheIleAsnLysAspThrGluThrIleAsnMetMetSer
GCTCCTCAGACACCTAGACCAGTGGCAGAAATTGTGCCATCCTTCATCAACAAAGATACAGAAACCATAAATATGATGTC

GluPheValAlaAsnLeuProGlnGluLeuLysLeuThrLeuSerGluMetGlnProAlaLeuProGlnLeuGlnGlnHis
AGAATTTGTTGCTAATTTGCCACAGGAGCTGAAGTTAACCCTGTCTGAGATGCAGCCAGCATTACCACAGCTACAACAAC

ValProValLeuLysAspSerSerLeuLeuPheGluGluPheLysLysLeuIleArgAsnArgGlnSerGluAlaAla
ATGTACCTGTATTAAAAGATTCCAGTCTTCTCTTTGAAGAATTTAAGAAACTTATTCGCAATAGACAAAGTGAAGCCGCA

AspSerSerProSerGluLeuLysTyrLeuGlyLeuAspThrHisSerArgLysLysArgGlnLeuTyrSerAlaLeuAla
GACAGCAGTCCTTCAGAATTAAAATACTTAGGCTTGGATACTCATTCTCGAAAAAAGAGACAACTCTACAGTGCATTGGC

AsnLysCysCysHisValGlyCysThrLysArgSerLeuAlaArgPheCys
TAATAAATGTTGCCATGTTGGTTGTACCAAAAGATCTCTTGCTAGATTTTGCTGAGATGAAGCTAATTGTGCACATCTCG

TATAATATTCACACATATTCTTAATGACATTTCACTGATGCTTCTATCAGGTCAATTCTCATGTTTGACAGCTTATCATC

GATAAGCTTTAATGCGGTAGTTTATCACAGTTAAATTGCTAACGCAGTCAGGCACCGTGTATGAAATCTAACAATGCGCT

CATCGTCATCCTCGGCACCGTCACCCTGGATGCTGTAGGCATAGGCTTGGTTATGCCGGTACTGCCGGGCCTCTTGCGGG

ATATCGTCCATTCCGACAGCATCGCCAGTCACTATGGCGTGCTGCTAGCGCTATATGCGTTGATGCAATTTCTATGCGCA

CCCGTTCTCGGAGCACTGTCCGACCGCTTTGGCCGCCGCCCAGTCCTGCTCGCTTCGCTACTTGGAGCCACTATCGACTA

CGCGATCATGGCGACCACACCCGTCCTGTGGATCC

FIG. 10A

```
GAATTCAACTTCTCCATACTTTGGATAAGGAAATACAGACATGAAAAATCTCATTGCTGAGTTGTTATTTAAGCTTGCCC
AAAAGAAGAAGAGTCGAAAGAACTGTGTGCGCAGGTAGAAGCTTTGGAGATTATCGTCACTGCAATGCTTCGCAATATG
GCGCAAAATGACCAACAGCGGGTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTAAAAAGTTAATCTTTTCAACA
GCTGTCATAAAGTTGTCACGGCCGAGACTTATAGTCGCTTTGTTTTATTTTTAATGTATTTGTACGCAAGTTCACGTA
                                               -23  Met Lys Lys Asn Ile Ala Phe Leu Leu Ala Ser Met
   trp S.D.        STII S.D.                         ATG AAA AAG AAT ATC GCA TTT CTT CTT GCA TCT ATG
AAAAGGGTATCTAGAGGTTGAGGTGATTTT
                                                          -20                    →
                                                                                  1
         -10
Phe Val Phe Ser Ile Ala Thr Asn Ala Tyr Ala Asp Ser Trp Met Glu Glu Val Ile Lys
TTC GTT TTT TCT ATT GCT ACA AAT GCC TAT GCA GAC TCA TGG ATG GAG GAA GTT ATT AAA
                                                                    20
 10
Leu Cys Gly Arg Glu Leu Val Arg Ala Gln Ile Ala Ile Cys Gly Met Ser Thr Trp Ser
TTA TGC GGC CGC GAA TTG GTA CGC GCG CAA ATA GCG ATA TGC GGT ATG AGT ACA TGG AGT

TGAAGAA
```

FIG. 16A

```
GAATTCAACTTCTCCATACTTTGGATAAGGAAATACAGACATGAAAAATCTCATTGCTGAGTTGTTATTTAAGCTTGCCC
AAAAAGAAGAAGAGTCGAAAGAACTGTGTGCGCAGGTAGAAGCTTTGGAGATTATCGTCACTGCAATGCTTCGCAATATG
GCGCAAAATGACCAACAGCGGTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTAAAAAGTTAATCTTTTCAACA
GCTGTCATAAAGTTGTCACGGCCGAGACTTATAGTCGCTTTGTTTTTATTTTTTAATGTATTTGTAACTAGTACGCAAGT
                                         -23           -20
     trp S.D.        STII S.D.      Met Lys Lys Asn Ile Ala Phe Leu Leu Ala
TCACGTAAAAAGGGTATCTAGAGGTTGAGGTGATTTT ATG AAA AAG AAT ATC GCA TTT CTT CTT GCA
     -10                                                  1
Ser Met Phe Val Phe Ser Ile Ala Thr Asn Ala Tyr Ala Ser Gly Thr Thr Asn Thr Val
TCT ATG TTC GTT TTT TCT ATT GCT ACA AAT GCC TAT GCA TCA GGC ACT ACA AAT ACT GTG
         10                                     20
Ala Ala Tyr Asn Leu Thr Trp Lys Ser Thr Asn Phe Lys Thr Ile Leu Glu Trp Glu Pro
GCA GCA TAT AAT TTA ACT TGG AAA TCA ACT AAT TTC AAG ACA ATT TTG GAG TGG GAA CCC
             30                                     40
Lys Pro Val Asn Gln Val Tyr Thr Val Gln Ile Ser Thr Lys Ser Gly Asp Trp Lys Ser
AAA CCC GTC AAT CAA GTC TAC ACT GTT CAA ATA AGC ACT AAG TCA GGA GAT TGG AAA AGC
             50                                     60
Lys Cys Phe Tyr Thr Thr Asp Thr Glu Cys Asp Leu Thr Asp Glu Ile Val Lys Asp Val
AAA TGC TTT TAC ACA ACA GAC ACA GAG TGT GAC CTC ACC GAC GAG ATT GTG AAG GAT GTG
             70                                     80
Lys Gln Thr Tyr Leu Ala Arg Val Phe Ser Tyr Pro Ala Gly Asn Val Glu Ser Thr Gly
AAG CAG ACG TAC TTG GCA CGG GTC TTC TCC TAC CCG GCA GGG AAT GTG GAG AGC ACC GGT
             90                                    100
Ser Ala Gly Glu Pro Leu Tyr Glu Asn Ser Pro Glu Phe Thr Pro Tyr Leu Glu Thr Asn
TCT GCT GGG GAG CCT CTG TAT GAG AAC TCC CCA GAG TTC ACA CCT TAC CTG GAG ACA AAC
            110                                    120
Leu Gly Gln Pro Thr Ile Gln Ser Phe Glu Gln Val Gly Thr Lys Val Asn Val Thr Val
CTC GGA CAG CCA ACA ATT CAG AGT TTT GAA CAG GTG GGA ACA AAA GTG AAT GTG ACC GTA
            130                                    140
Glu Asp Glu Arg Thr Leu Val Arg Arg Asn Asn Thr Phe Leu Ser Leu Arg Asp Val Phe
GAA GAT GAA CGG ACT TTA GTC AGA AGG AAC AAC ACT TTC CTA AGC CTC CGG GAT GTT TTT
            150                                    160
Gly Lys Asp Leu Ile Tyr Thr Leu Tyr Tyr Trp Lys Ser Ser Ser Gly Lys Lys Thr
GGC AAG GAC TTA ATT TAT ACA CTT TAT TAT TGG AAA TCT TCA AGT TCA GGA AAG AAA ACA
            170                                    180
Ala Lys Thr Asn Thr Asn Glu Phe Leu Ile Asp Val Asp Lys Gly Glu Asn Tyr Cys Phe
GCC AAA ACA AAC ACT AAT GAG TTT TTG ATT GAT GTG GAT AAA GGA GAA AAC TAC TGT TTC
            190                                    200
Ser Val Gln Ala Val Ile Pro Ser Arg Thr Val Asn Arg Lys Ser Thr Asp Ser Pro Val
AGT GTT CAA GCA GTG ATT CCC TCC CGA ACA GTT AAC CGG AAG AGT ACA GAC AGC CCG TAT
            210                                    220
Glu Cys Met Gly Gln Glu Lys Gly Glu Phe Arg Glu Ile Phe Lyr Ile Ile Gly Ala Val
GAG TGT ATG GGC CAG GAG AAA GGG GAA TTC AGA GAA ATA TTC TAC ATC ATT GGA GCT GTG
            230                                    240
Val Phe Val Val Ile Ile Leu Val Ile Ile Leu Ala Ile Ser Leu His OC*
GTA TTT GTG GTC ATC ATC CTT GTC ATC ATC CTG GCT ATA TCT GTA CAC TAA AATTCTCATGT
TTGACAGCTTATCATCGATCAGCTTTAATGCGGTAGTTTATCACAGTTAAATTGCTAACGCAGTCAGGCACCGTGTATGA
AATCTAACAATGCGCTCATCGTCATCCTCGGCACCGTCACCCTGGATGCTGTAGGCATAGGCTTGGTTATGCCGGTACTG
CCGGGCCTCTTGCGGGATATCGTCCATTCCGACAGCATCGCCAGTCACTATGGCGTGCTGCTAGCGCTATATGCGTTGAT
GCAATTTCTAT
```

FIG. 18B

MetLysSerAsnAsnAlaLeuIleValIleValIleLeuGlyThrValThrLeuAspAlaValAlaGlyIleGlyLeuValMet
AAGCTTATGAAATCTAACAATGCGCTCATCGTCATCGTCATCCTCGGCACCGTCACCCTGGATGCTGTAGGCATAGGCTTGGTTAT

ProValLeuProGlyLeuLeuArgAspIleValHisSerAspSerIleAlaSerHisTyrGlyValLeuLeuAlaAlaLeuTyr
GCCGGTACTGCCGGGCCTCTTGCGGGATATCGTCCATTCCGACAGCATCGCCAGTCACTACTATGGCGTGCTGCTAGCGCTAT

AlaLeuMetGlnPheLeuCysAlaProValLeuGlyAlaLeuSerAspArgPheGlyArgArgProValLeuLeuAla
ATGCGTTGATGCAATTTCTATGCGCCAGTCCTTGGAGCACTGTCCGACCGCTTTGGCCGCCGCCCAGTCCTCCTGCTCGCT

SerLeuLeuGlyAlaThrIleAspTyrAlaIleMetAlaThrThrProValLeuTrp
TCGCTACTTGGAGCCACTATCGACTACGCGGATCATGGGGACCACACCCGTCCTGTGGATCC

PROCESS FOR PRODUCING RELAXIN

This is a continuation of application Ser. No. 08/080,354, filed Jun. 21, 1993 now abandoned.

FIELD OF THE INVENTION

This invention relates to non-naturally occurring forms of prorelaxin and to a process for producing relaxin from such a non-naturally occurring form of prorelaxin.

BACKGROUND OF THE INVENTION

Mature human relaxin is an ovarian hormonal peptide of approximately 6000 daltons in molecular weight known to be responsible for remodeling the reproductive tract before parturition, thus facilitating the birth process. The protein appears to modulate the restructuring of connective tissues in target organs to obtain the required changes in organ structure during pregnancy and parturition. Some of the important roles for relaxin as a pregnancy hormone include inhibition of premature labor, cervical ripening at parturition, and development of the mammary gland [Reddy et al., Arch. Biochem. Biophys. 294, 579 (1992)]. While predominantly a hormone of pregnancy, relaxin has also been detected in the non-pregnant female as well as in the male (seminal fluid).

The amino acid sequences of relaxin have been determined by direct protein sequencing or deduced from the nucleotide sequences of the DNAs for a number of species including pig, rat [Hudson, et al. Nature 291, 127 (1981)], sand tiger shark, spiny dogfish, skate, whale, monkey and human. [Hudson et al. EMBO J. 3, 2333 (984)]

Recombinant techniques were first applied to the isolation of CDNA clones for rat and porcine relaxins (Hudson, et al., Nature vol. 291, pg. 544 [1981]; Haley et al., DNA vol. 1, pg. 155 [1982]). Two human gene forms have been identified by genomic cloning using probes from the porcine relaxin gene (Hudson et al., Nature vol. 301, pg. 628 [1983]; Hudson et al., EMBO J. vol. 3 pg 2333 [1984]; U.S. Pat. Nos. 4,758,516 [issued 19 Jul. 1988] and 4,871,670 [issued 3 Oct. 1989], although only one of these gene forms (termed H2) has been found to be transcribed in corpora lutea. It is unclear whether the other gene is expressed at another tissue site or whether it represents a pseudo-gene. The fact that H2 relaxin is synthesized and expressed in the ovary suggests that this is the sequence that is directly involved in the physiology of pregnancy.

Naturally occurring relaxin is synthesized as a single-chain 23 kDa preprorelaxin with the overall structure: signal peptide, B-chain, connecting C-peptide, and A-chain. During the biosynthesis of relaxin, the signal peptide is removed as the nascent chain is moved across the endoplasmic reticulum producing the 19-kDa prorelaxin (Reddy et al., Supra). Further processing of the prorelaxin to relaxin occurs in vivo through the endoproteolytic cleavage of the C-peptide at specific pairs of basic amino acid residues located at the B/C-chain and A-/C-chain junctions after the formation of disulfide bridges between the B- and A-chains (Marriott et al. Mol. Endo. vol. 6 no. 9 [1992]) in a manner analogous to insulin. The relaxin disulfide bridges occur between the cysteines at A9-B10 and A22-B22 with an intra-chain disulfide bridge within the A-chain between A8 and A13 (U.S. Pat. No. 4,656,249, issued Apr. 7, 1987).

A concise review of the knowledge about relaxin as of 1988 was provided by Sherwood, D. in The Physiology of Reproduction Chapter 16, "Relaxin", Knobil, E. and Neill, J. et al., (eds.) Raven Press, Ltd. New York pp. 585–673 [1988]. Relaxin has been consistently associated with the condition of pregnancy, and most of its known utilities are associated with this condition.

H2 relaxin has been described to remodel the reproductive tract to facilitate the birth process, including ripening of the cervix, thickening of the endometrium of the pregnant uterus as well as increased vascularization to this area, and an effect on collagen synthesis. H2 relaxin has also been associated with lactation, and some reports indicate that relaxin has a growth-promoting effect on mammary tissue (Wright, L. C. and Anderson, R. R., Adv. Exp. Med. Biol. vol 341 [1982]). Given the effect of relaxin on the connective tissue, it has been suggested that relaxin may improve skin elasticity. U.S. Pat. No. 5,166,191, issued 21-Feb-1992, describes the use of relaxin in cardiovascular therapy.

U.S. Pat. No. 5,023,321, issued Jun. 11, 1991, discloses the preparation of human preprorelaxin and sub-units thereof. U.S. Pat. No. 4,871,670, issued Oct. 3, 1989, discloses genes and DNA transfer vectors for the expression of human preprorelaxin and sub-units thereof.

European Pat. Publ. Nos. 101,309 published Feb. 22, 1984 and 112,149 published Jun. 27, 1984 respectively disclose the molecular cloning and characterization of a gene sequence coding for human relaxin and human H2-relaxin and analogs thereof.

U.S. Pat. No. 4,565,249, issued Apr. 7, 1987, discloses a method for the synthesis of porcine relaxin or modified forms or analogues thereof. Australian Pat. No. 561,670 issued Aug. 26, 1987, and Haley et al., DNA 1:155–162 (1982) disclose how to prepare porcine relaxin and Stewart et al., NAR vol. 11, no. 19 pg. 6597–6609 (1983) disclose expression of porcine prorelaxin in E. coli. Reddy et al., Supra, disclose a method for purification of a recombinant porcine prorelaxin expressed in E. coli.

Gold et al., (Abstr. Pap. Chem. Soc. 203 Meet., Pt. 3, BTEC55 [1992]) disclose a method for the production of relaxin based on the A-chain B-chain combination reaction. The A-chain was expressed in E. coli as a modified prorelaxin in retractile bodies; the A-chain was purified from the modified prorelaxin by chemical cleavage. The B-chain was produced in a second E. coli fermentation in which it was secreted and subsequently purified. The two purified chains were then combined in an oxidative combination and folding reaction. During the reaction, 1 intrachain disulfide and 2 interchain disulfide bonds were formed. The two-chain combination process involves numerous process steps and the use of dual fermentations for production of the two chains.

Marriott et al., [Molecular Endocrinology 6, 1441 (1992)] disclose mammalian expression of a prorelaxin variant having non-naturally occurring cleavage sites at the A-/C-chain and B-/C-chain junctions.

Recombinant Expression

There exists a need for a process for producing relaxin from prorelaxin that does not require the use of dual fermentation and numerous process steps as is used for the two-chain combination process. There exists a need for a prorelaxin product recovery process that will provide large enough yields of biologically active relaxin to be commercially feasible. There exists a need for an isolated prorelaxin that can be expressed in a prokaryotic system and subsequently processed to biologically active relaxin not contaminated with host generated materials or other recombinant artifacts that reduce biological activity.

SUMMARY OF THE INVENTION

The present invention is based on the unexpected experimental finding that biologically active relaxin in commercially effective amounts and purity can be produced via non-naturally occurring prorelaxin forms. The present invention is based on the unexpected experimental finding that non-naturally occurring prorelaxin forms are successfully folded and processed to biologically active relaxin in recombinant systems in greater yields than realized using naturally occurring prorelaxin.

The present invention is based on the design and construction of nonnaturally occurring prorelaxin forms having a leader sequence, a B-chain, a non-naturally occurring C-peptide, and an A-chain. The leader sequence is comprised of a cleavage site adjacent to the prorelaxin B-chain, and the non-naturally occurring C-peptide is comprised of a cleavage site at the B-chain/C-chain junction and the A-chain/C-chain junction. The present invention is also based on the design of a product recovery process for the production of biologically active relaxin from a non-naturally occurring prorelaxin.

The present invention is accomplished by providing a process for producing relaxin from fermentation of a non-naturally occurring prorelaxin which method comprises:

(a) providing nucleic acid encoding the non-naturally occurring prorelaxin, wherein the prorelaxin comprises a leader sequence, a B-chain, a non-naturally occurring C-chain, and an A-chain, and wherein said leader sequence comprises a first cleavage site adjacent the B-chain sequence and wherein said non-naturally occurring C-chain comprises second and third cleavage sites adjacent the B-chain and the A-chain, respectively; (b) culturing prokaryotic cells containing said nucleic acid encoding said non-naturally occurring prorelaxin, the culturing resulting in expression of said nucleic acid to produce said non-naturally occurring prorelaxin in said prokaryotic cell; (c) isolating and solubilizing said prorelaxin produced by said culturing method; (d) refolding said solubilized prorelaxin; (e) excising said leader sequence and said non-naturally occurring C-peptide from said prorelaxin, wherein excision is accomplished through the use of cleaving agents specific for said cleavage sites; and (f) recovering relaxin. The process may further comprise cyclizing the A-chain N-terminal glutamine.

In a preferred embodiment of the present invention, the relaxin is human relaxin of the H2 form.

In one embodiment of the present invention, the excision of the leader sequence and non-naturally occurring C-peptide is through enzymatic cleavage.

In one embodiment of the present invention, the excision of the leader sequence and non-naturally occurring C-peptide is accomplished through the use of trypsin and carboxypeptidase B (CPB), and in another embodiment, Arg C and CPB. The excision of the leader sequence is preferably accomplished through the use of endoproteinases AspN and trypsin. The excision of the non-naturally occurring C-peptide is preferably accomplished through the use of Arg C, trypsin or Lys C with carboxypeptidase B, or with trypsin and Arg C. See FIGS. 2A–2D.

In one embodiment of the present invention, the solubilized prorelaxin is refolded under conditions of dilute protein concentration. In another embodiment of the present invention, the solubilized prorelaxin may be refolded under controlled oxidation conditions.

In another aspect, the present invention provides an isolated prorelaxin comprising a leader sequence, a B-chain, a non-naturally occurring C-peptide, and an A-chain.

BRIEF DESCRIPTION OF THE DRAWINGS

FIG. 1 shows the makeup of DNA encoding a prorelaxin hereof including a non-naturally occurring leader ("ST II") (SEQ ID NO:1) and C-peptide ("mini C") and having cleavage sites after the leader and between the C-peptide (SEQ ID NO:3) and B (SEQ ID NO:2) and A chains as identified.

FIGS. 2A,2B,2C,2D and 2E show the leader sequence, the non-naturally occurring C-peptide, and the enzymatic cleavage sites for four constructs of the present invention. (Sequence I.D. nos. 5–8)

FIG. 3 shows the nucleic acid (SEQ ID NO:9) and amino acid (SEQ ID NO:10) sequence for the plasmid pRB250CTsc. See also FIG. 1.

FIG. 9B illustrates the Not I-Bam HI fragment (SEQ ID NO:11 and SEQ ID NO:12) from pTR21.

FIG. 10A provides a partial sequence (SEQ ID NO:13 and SEQ ID NO:14) of plasmid pRB11. (Sequence I.D. no. 10)

FIG. 16A provides a partial sequence (SEQ ID NO:15 and SEQ ID NO:16) of pTF271, an intermediate in the construction of pRB61. (Sequence I.D. no. 11)

FIG. 18B illustrates the sequence (SEQ ID NO:17 and SEQ ID NO:18) of the 291bp Hind III-Bam HI fragment from pLS8.

DETAILED DESCRIPTION OF THE INVENTION

Figure 2E:
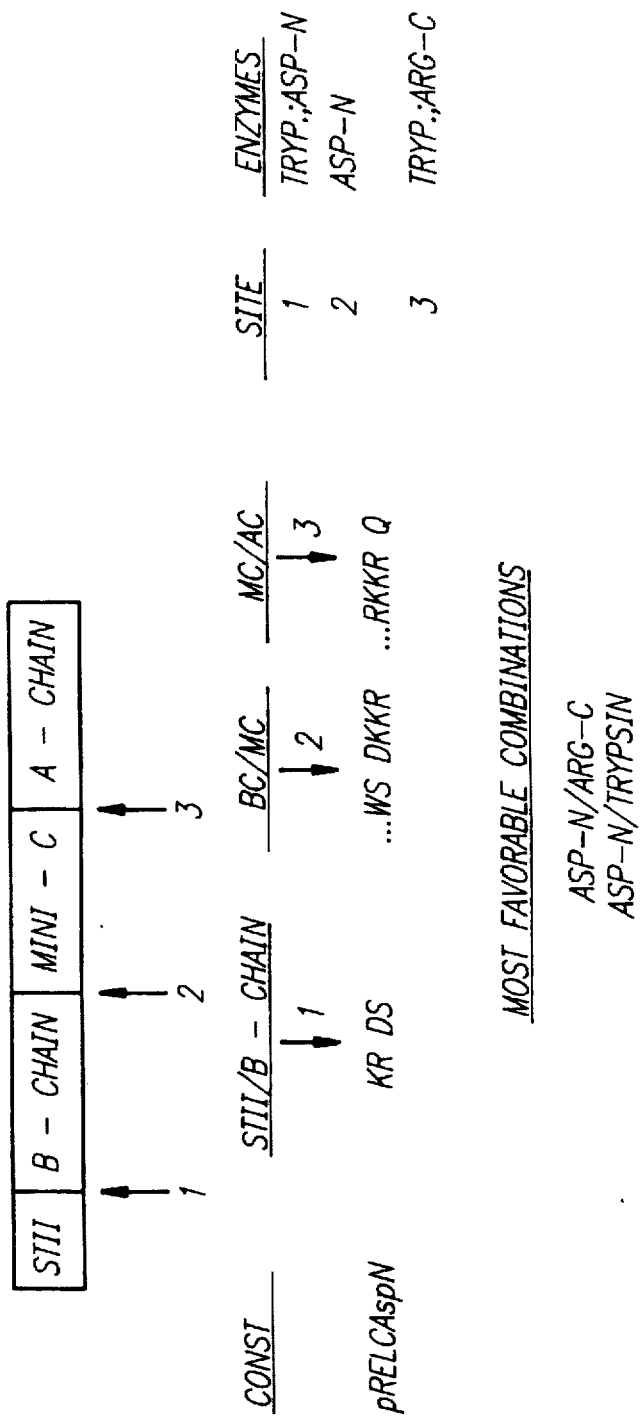

As used herein, "relaxin" is defined as a polypeptide having the amino acid sequence described in Hudson et al., (*EMBO J.* 3, 2333 [1984]) together with naturally occurring amino acid sequence variants, such as naturally occurring alleles thereof, which retain the qualitative biological activity of relaxin.

Also falling within the scope of the present invention are nonnaturally occurring relaxin amino acid substitutions, insertions or deletions, such as those that can be introduced using recombinant DNA technology, and covalent or non-covalent relaxin modifications, for example glycosylation modifications, provided that the final relaxin possesses the qualitative biological activity of naturally occurring relaxin.

The term relaxin refers as well to various forms of human and non-human animal relaxin as known to be biologically active in accepted relaxin assays such as the pubic symphysis in vitro bioassay [Steinetz et al., *Endocrinology* 67, 102 (1960)], the rat uterine smooth muscle in vitro assay (St. Louis, [*J. Can J. Physiol. Pharmacol.* 59, 507 (1981)] and measurement of cAMP levels after hormonal stimulus (Braddon, S. A., [*Endocrinology* 102, 1292 (1978)] and Judson et al., [*J. Endocrinology* 87, 153 (1980)].

Prorelaxin as used herein refers to the precursor of relaxin that comprises the B-, A-, and C-chains, "relaxin" being as defined above. A feature of the prorelaxins hereof is that they contain a non-naturally occurring C-chain, as defined further infra.

The prorelaxin precursor of the present invention is meant to include prorelaxin obtained from a natural source, chemically synthesized, or produced by techniques of recombinant DNA technology. Certain of the non-naturally occurring prorelaxins of the present invention have non-naturally occurring C-chains connecting naturally occurring A- and B-chains. Some of the non-naturally occurring prorelaxins of the present invention have non-naturally occurring C-chains comprised of naturally occurring enzyme cleavage sites, whereas other non-naturally occurring prorelaxins are comprised of non-naturally occurring enzyme cleavage sites.

The term "C-chain" as used herein refers to the peptide which connects the A and B chains of prorelaxin. A focus of the present invention is the use of "non-naturally occurring C-chain" defined herein as a peptide connecting the A and B chains of prorelaxin that does not occur in the natural protein. The preferred non-naturally occurring C-chain of the present invention is a peptide that connects the A and B chain of prorelaxin and is comprised of amino acids encoding cleavage sites at the B-/C-chain junction and the A-/C-chain junction. Preferred are C-chains having about 8 to 15 amino acids.

The term prorelaxin "leader", "leader peptide", "leader sequence" or "signal sequence" as used herein refers to the short amino acid sequence that is found at the N-terminus of the prorelaxin hereof. The preferred leader sequence herein is non- or semi-functional in directing prorelaxin to the periplasm of the host prokaryotic cell. Prorelaxin produced by the host cells of the present invention is typically found in and purified from so-called refractile bodies. A particularly preferred leader sequence of the present invention is a truncated STII leader sequence that is used to drive high expression of the prorelaxin, rather than necessarily to achieve secretion of prorelaxin into the periplasm of the host cell. Typically, Lys and Arg are included in the "leader sequence" of the present invention to allow for cleavage of the leader sequence from relaxin.

A typical leader, illustrated as a model herein, is defined as MKKNIAFLLKR (SEQ ID NO:1). Equivalents thereof would include MKKNIAFLLRK (SEQ ID NO:19), MKKNIAFLLRR (SEQ ID NO:20) and MKKNIAFLLKK (SEQ ID NO:21). An attendant feature for a useful leader is that it contain a proteolytic enzyme cleavage site for cleavage from the B-chain.

As used herein the phrase "process for producing relaxin from prorelaxin" or "product recovery process for the production of relaxin" refers to the design and construction of non-naturally occurring prorelaxin as well the fermentation process for culturing prorelaxin and any subsequent steps for purifying relaxin. Steps for purifying relaxin from prorelaxin expressed in a host culture include but are not limited to, isolating prorelaxin retractile bodies, such as by centrifuging, solubilizing the prorelaxin, refolding the solubilized prorelaxin, cleaving the prorelaxin leader sequence and C-peptide, removing impurities from the relaxin, and providing the relaxin in a form for final formulation. These purification steps are illustrative rather than limiting.

The term "commercially feasible or effective yields or amounts" refers to final relaxin yields derived from the prokaryotic fermentation of a prorelaxin hereof and is defined as being at least about 10 to 100 mg/L, and preferably, greater than about 100 mg/L.

The terms "biological activity", and grammatical equivalents refer to any biological activities exhibited by wild-type human relaxin. The relaxin biological activity may, for example, be determined in accepted relaxin assays such as the pubic symphysis in vitro bioassay [Steinetz et al., *Endocrinology* 67, 102 (1960)], the rat uterine smooth muscle in vitro assay (St. Louis, [*J. Can J. Physiol. Pharmacol.* 59, 507 (1981)] and measurement of cAMP levels after hormonal stimulus (Braddon, S. A., [*Endocrinology* 102, 1292 (1978)] and Judson et al., [*J. Endocrinology* 87, 153 (1980)].

The term "cleaving agent" as used herein refers to a reagent used to cleave the prorelaxin hereof specifically so as to release or excise certain components, such as the leader sequence or the C-peptide, as desired. Suitable cleaving agents herein include enzymes, such as endoproteases, e.g., endoproteinase Lys C, endoproteinase Arg C, endoproteinase Asp N; trypsin; carboxypeptidase B; prohormone convertase (PC), e.g., furin, PC1, PC2, KEX2; subtilisin, or its mutants; and chemical agents, such as organic or inorganic acids, hydroxylamine, N-bromosuccinimide, and cyanogen bromide.

Hydrolysis of peptide bonds catalyzed by a variety of proteolytic enzymes is taught in *The Enzymes*, 3rd ed., Boyer, Ed., Academic Press, Vol. III, [1971]; *Meth. Enzymol.* Vol. XIX, Perlman and Lorand, Ed. New York: Academic Press [1970]; *Enzymol.* Vol. XLV, Lorand, Ed. New York: Academic Press [1976]; Drapeau, [*J. Biol. Chem.* 253: 5899 (1978)] and Drapeau, [*Meth. Enzymol.* 47, 89 (1977)]. For an extensive listing of chemical agents, see Witcop in *Advances in Protein Chemistry*, Anfinsen et al., ed., Vol 16 pg. 221-321, Academic Press, New York [1961], including Table III on p. 226.

Other cleavage agents suitable herein are deemed to be understood by those skilled in the art keeping in mind the desired junction for cleavage and whether the reagent can act on reduced or oxidized forms of prorelaxin. Conditions used for cleavage of the non-naturally occurring prorelaxin will depend upon the cleaving agent employed, and the conditions will be readily apparent to one skilled in the art given the cleavage agent employed.

In the present invention, the non-naturally occurring prorelaxin is designed and constructed to comprise the codon(s) necessary to achieve cleavage by the desired cleaving agent at desired position or positions, i.e., after a leader sequence or to excise a C-peptide. It may be necessary to insert the appropriate codons either upstream and preferably adjacent to the 5'-terminal codon of the sequence encoding the desired polypeptide component, in this case relaxin B-chain or A-chain, or downstream, and preferably adjacent to the carboxy terminal codon of the desired component of the polypeptide, or both if the desired component to be isolated is an internal amino acid sequence of the expected translation product.

In the present invention, it is efficient that the prorelaxin leader sequence and C-peptide are excised by the same cleavage method. Any enzyme or chemical that can cleave the cleavage sites available at the leader sequence/B-chain junction, the B-/C-chain junction and the A-/C-chain junction can be used as long as the desired hormone, relaxin, can be generated.

The oligonucleotides are readily synthesized using techniques well known in the art such as that described by Crea et al., *Proc. Nat'l. Acad. Sci. USA* 75:5765 (1978), or Kunkel et al., *Methods in Enzymol.* 154 367 (1987).

Mutants with more than one amino acid substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Another method for making mutations in the nucleic acid sequence encoding wild-type prorelaxin or a variant molecule known in the art, involves cleaving the nucleic acid sequence encoding the starting prorelaxin molecule at the appropriate position by digestion with restriction enzymes, recovering the properly cleaved nucleic acid, synthesizing an oligonucleotide encoding the desired amino acid sequence and flanking regions such as polylinkers with blunt ends (or, instead of polylinkers, digesting the synthetic oligonucleotide with the restriction enzymes also used to cleave the prorelaxin encoding nucleic acid, thereby creating cohesive termini), and ligating the synthetic nucleic acid into the remainder of the prorelaxin encoding structural gene.

PCR mutagenesis is also suitable for making the prorelaxin variants of the present invention, for example, as described in U.S. Pat. No. 4,683,195, issued 28 Jul. 1987, and in *Current Protocols in Molecular Biology*, Ausubel et al., eds. Greene Publishing Associates and Wiley-Interscience, Volume 2, Chapter 15, 1991. While the following discussion refers to DNA, it is understood that the technique also finds application with RNA. Mutations at separate positions can be introduced simultaneously by either using a mutant second primer or performing a second PCR with different mutant primers and ligating the two resulting PCR fragments simultaneously to the vector fragment in a three (or more)-part ligation.

The relaxin nucleic acid derived from RNA, cDNA, genomic DNA, synthetic DNA or a combination of DNA is inserted into a replicable vector for further cloning (amplification of the nucleic acid) or for expression. Construction of suitable vectors containing the desired coding and control sequences employs standard recombinant techniques. Isolated plasmids or nucleic acid fragments are cleaved, tailored, and religated to form the desired plasmid.

Many vectors are available, and selection of the appropriate vector will depend on 1) whether it is to be used for nucleic acid amplification or for nucleic acid expression, 2) the size of the nucleic acid to be inserted into the vector, and 3) the host cell to be transformed with the vector. Each vector contains various components depending on its function (amplification of nucleic acid or expression of nucleic acid) and the host cell for which it is compatible. The vector components generally include, but are not limited to, one or more of the following: a signal sequence, an origin of replication, one or more marker genes, an enhancer element, a promoter, and a transcription termination sequence.

The preferred replicable vector of the present:

invention is one containing a leader sequence that allows for expression of the non-naturally occurring prorelaxin and correct N-terminal processing of the prorelaxin B-chain, the tryptophan (trp) promoter, the lambdas termination sequence, a PBR322 origin of replication, an antibiotic resistance gene and the relaxin A and B chains connected by a non-naturally occurring C-peptide wherein said C-peptide is comprised of enzymatic cleavage sites at the B-/C-chain and A/C-chain junction.

Prokaryotes are the preferred host cells for the initial cloning steps of prorelaxin. They are particularly useful for rapid production of large amounts of nucleic acid, for production of single-stranded nucleic acid templates used for site-directed mutagenesis, for screening many mutants simultaneously, and for nucleic acid sequencing of the mutants generated. Examples of prokaryotes, e.g. *E. coli* , and expression vectors, suitable for use in producing prorelaxin are, for example, those disclosed in WO 90/02798 (published 22 Mar. 1990).

Prokaryotes used for cloning of prorelaxin DNA sequences also include for example, *E. coli* K12 strain 294 (ATCC No. 31446), *E. coli* B, and *E. coli* X1776 (ATCC No. 31537).

Prokaryotes also are used for expression. Suitable host cells for cloning or expressing the vectors herein are the *E. coli* cells. *E. coli* strain W3110 (F-, 1-, prototrophic, ATCC No. 27325) is a particularly preferred parent host because it is a common host strain for recombinant DNA product fermentations. Preferably, the host cell should secrete minimal amounts of proteolytic enzymes. Strain W3110 may be modified to effect a genetic mutation in the genes encoding proteins, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 Δ(argF-lac)169 ompTΔ degP41kan'; *E. coli* W3110 strain 37D6, which has the complete genotype TonAΔ ptr3 phoAΔE15 4(argF-lac)169 ompTΔ degP41kan'rbs7ΔilvG; *E. coli* strain W3110 strain 40B4m which is strain 37D6 with a non-kanamycin resistant degP deletion mutation; and an *E. coli* strain having mutant periplasmic protease disclosed in U.S. Pat. No. 4,946,783, issued 7 Aug. 1990.

Cloning and expression methodologies are well known in the art and are, for example, disclosed in the foregoing published PCT patent application (WO90/02798).

Fermentation of the prorelaxin is carried out through methodologies well known in the art and are, for example, disclosed in Elander (*Genetic Engineering Technology in*

*Industrial Pharmacy* edited by John M. Tabor, published by Marcel Dekker, Inc. pg. 115–129 [1989]), however many fermentation variables exist which remain to be optimized for each fermentation process. The major goals of fermentation development are to optimize cell mass and maximize product accumulation. Large scale fermentation refers to fermentation in a fermentor that is at least approximately 1000 liters in volumetric capacity, i.e., working volume, leaving adequate room for headspace. Small scale fermentation refers generally to fermentation in a fermentor that is no more than approximately 100 liters in volumetric capacity, preferably no more than approximately 10 liters.

Isolation of crude product from the fermentation broth can be accomplished by the use of filtration, centrifugation, and/or settling, sedimentation and decanting or a combination of techniques. Isolation of crude product in the form of retractile bodies requires a first step of cell disruption in order to release the refractile body from the cell. Methods of cell disruption include sonication, passage through homogenizers, and cell lysis accomplished through the use of lysozyme, detergent or other agents.

Once the refractile bodies are released from the cell, the bodies may be separated from the remaining fermentation solution based on differences in physical and chemical properties such as size and solubility. Sedimentation refers to settling in a simple gravitational field, whereas centrifugation requires production of enhanced settling velocities by centrifugal forces. In the present invention, the preferred manner of isolating crude prorelaxin from the fermentation broth includes a form of mechanical cell disruption, to release the prorelaxin refractile body from the cell, followed by any centrifugal technique which allows for separation of refractile bodies from light solid wastes and liquids. In the present invention, the preferred form of mechanical cell disruption is by homogenization while the preferred centrifugal technique is a high volume, continuous flow, solid bowl centrifugation.

In the case where proteins are expressed in the form of intracellular refractile bodies, the product recovery process will include process steps for solubilizing the refractile bodies, renaturing the solubilized protein and where appropriate, a controlled oxidation step to obtain useful product. After isolation of crude prorelaxin refractile bodies from the fermentation broth, the prorelaxin refractile bodies are solubilized and refolded.

Solvents used to solubilize the protein in refractile bodies include, but are not limited to, Guanidine-HCl (GuHCl) (up to 8M), Urea (up to 8M), SDS, Alkaline pH (>8.0), acid pH (<3.0) and Acetonitrile/propanol. The referred solubilization buffer for the prorelaxin efractile bodies of the present invention is GuHCl, 3.5–4.0M or Urea, 2–8M. In the present invention, PEI (polyethyleneimine) is used to retain prorelaxin in a soluble form while precipitating contaminants.

Refolding of solubilized protein can be accomplished by lowering or removing the solubilizing agent (e.g., by dialysis or dilution) with oxidation of reduced protein occurring prior to or concomitant with refolding for proteins containing disulfide bridges. In the present invention, it is preferred that the folding step take place in an oxidative environment using a redoxo buffer. In the present invention it is preferred that refolding be carried out at as dilute a concentration as feasible, taking into consideration workable volumes of solutions and possible loss due to high dilution for subsequent purification steps. It is most preferred to use dilutions in the range of 60–100 times refractile body weight in grams. During the solubilization and refolding process, it is also preferable to minimize exposure to conditions which result in derivatization of prorelaxin amino acid side chains (e.g., prolonged exposure to pH values of greater than 9.0). For refolding proteins, such as prorelaxin, that contain cysteine residues and in the naturally occurring form contain disulfide bonds, the reduction/oxidation conditions present in the solubilization and refolding steps are critical and protein specific. In the present invention it is preferred that the steps of solubilization and refolding take place at 2°–80° C.

After refolding, purification processes are necessary to remove other proteins, contaminating nucleic acids present in the inclusion body, and folding intermediates and to isolate and concentrate the prorelaxin. The following examples are exemplary of suitable purification procedures: fractionation on immunoaffinity or ion-exchange columns; ethanol precipitation; reverse phase HPLC; chromatography on silica columns; electrophoresis; ammonium sulfate precipitation; gel filtration; ultrafiltration/diafiltration; metal chelate chromatography; and hydrophobic interaction chromatography. Chromatographic matrices are commercially available for use in purification of desired product from contaminants; a review of chromatographic matrices is given in Marston et al., Supra and Section VII from [*Guide to Protein Purification* edited by Deutscher, published by Academic Press, Inc. 309 (1990)].

In the present invention, it is preferred that the cleavage of prorelaxin to relaxin take place after prorelaxin refolding and subsequent removal of solubilizing agents. Methods of cleavage include chemical cleavage and enzymatic cleavage as discussed herein.

In the present invention, the preferred process includes a process step for cyclization of the relaxin A-chain N-terminal glutamine. Any process for cyclization of the A-chain N-terminal glutamine can be used. Examples of such a process are heat treatment, preferably under slightly acidic conditions, and treatment with nucleophilic reagents, such as imidazole at neutral pH. Any process steps used to cyclize the N-terminal A chain may require additional purification steps to remove any contaminants caused by the cyclization procedure itself, and may include centrifugation, column chromatography or precipitation techniques.

Final product purification may include steps of chromatography, organic solvent removal, ultrafiltration/diafiltration which provide relaxin in a form for final formulation.

Typically, the relaxin used in the method of this invention is formulated by mixing it at ambient temperature at the appropriate pH, and at the desired degree of purity, with pharmaceutically acceptable carriers, i.e., carriers that are non-toxic to recipients at the dosages and concentrations employed. Suitable carriers and their formulations are described in *Remington's Pharmaceutical Sciences*, 16th ed., 1980, Mack Publishing Co., edited by Oslo et al. These compositions will typically contain an effective amount of the relaxin, for example, from on the order of about 0.0003 upwards of about 8 or more mg/ml, together with a suitable amount of carrier to prepare pharmaceutically acceptable compositions suitable for effective administration to the patient.

The pH of the formulation preferably ranges anywhere from about 3 to about 8. Formulation in an acetate buffer at pH 5 is a suitable embodiment. The preferred formulation for relaxin is a buffered or unbuffered solution, and is preferably 20 mM sodium acetate, pH 5.0.

Compositions particularly well suited for the clinical administration of relaxin include sterile aqueous solutions or sterile hydratable powders such as lyophilized protein. Typically, an appropriate amount of a pharmaceutically acceptable salt is also used in the formulation to render the formulation isotonic.

Sterility is readily accomplished by sterile filtration through (0.2 micron) membranes. Relaxin ordinarily will be stored as an aqueous solution, although lyophilized formulations for reconstitution are acceptable.

The relaxin composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of relaxin to be administered will be governed by such considerations, and is the minimum amount necessary to prevent, ameliorate, or treat the disorder.

As a general proposition, the pharmaceutically effective amount of the relaxin administered per dose will be in the range of about 0.001 to 100 mg/kg of patient body weight per day with the typical range of relaxin used being 0.005 to 50 mg/kg/day.

The invention will be more fully understood by reference to the following examples. They should not, however, be construed as limiting the scope of the invention. All literature citations are expressly incorporated by reference.

EXAMPLE 1

Construction of Expression Vehicle for a Model of Non-Naturally Occurring Prorelaxin The plasmid pRB250CTsc is comprised of prorelaxin (the relaxin A and B chains derived from the sequence disclosed in Hudson et al., [EMBO J. 3, 2333 (1984)] having a non-naturally occurring leader sequence and a non-naturally occurring C-peptide containing trypsin and trypsin/carboxypeptidase enzymatic cleavage sites at the A/C chain junction and the B/C chain junction, as is shown in FIGS. 1 and 3. The transcriptional and translational sequences required for expression of the prorelaxin gene in E. coli are provided by the tryptophan (trp) promoter derived from pHCH207-1 (deBoer et al., from [Promoters: Structure and Function, eds. Rodriguez and Chamberlain, publisher M. J. Praeger, New York 462 (1982)]. The lambda $t_o$ transcriptional terminator [Scholtisses, et al., NAR 15, 3185 (1987)] is situated adjacent to the prorelaxin termination codon. Plasmid pRB250CTsc confers tetracycline resistance upon the transformed host. Plasmid pRB250CTsc has an origin of replication from a pBR322 vector [Sutcliff, Cold Spring Harbor symposium on quantitative Biology 43, 77 (1978)].

Plasmid pRB250CTsc also has 9 amino acids from the E. coli heat-stable enterotoxin II (STII) gene [Picken et al., Infect. Immun. 42, 269 (1983)] followed 3' by amino acids Lys and Arg.

The STII 9 amino acids plus Lys and Arg are located 3' to the Trp promoter and allow for high level expression of the non-naturally occurring prorelaxin having a convenient cleavage site provided, thereby allowing for generation of the correct N-terminal processing of the prorelaxin B-chain through enzymatic cleavage. The STII 9 amino acids do not encode a functional leader sequence.

Plasmid pRB250CTsc

Figure 4:
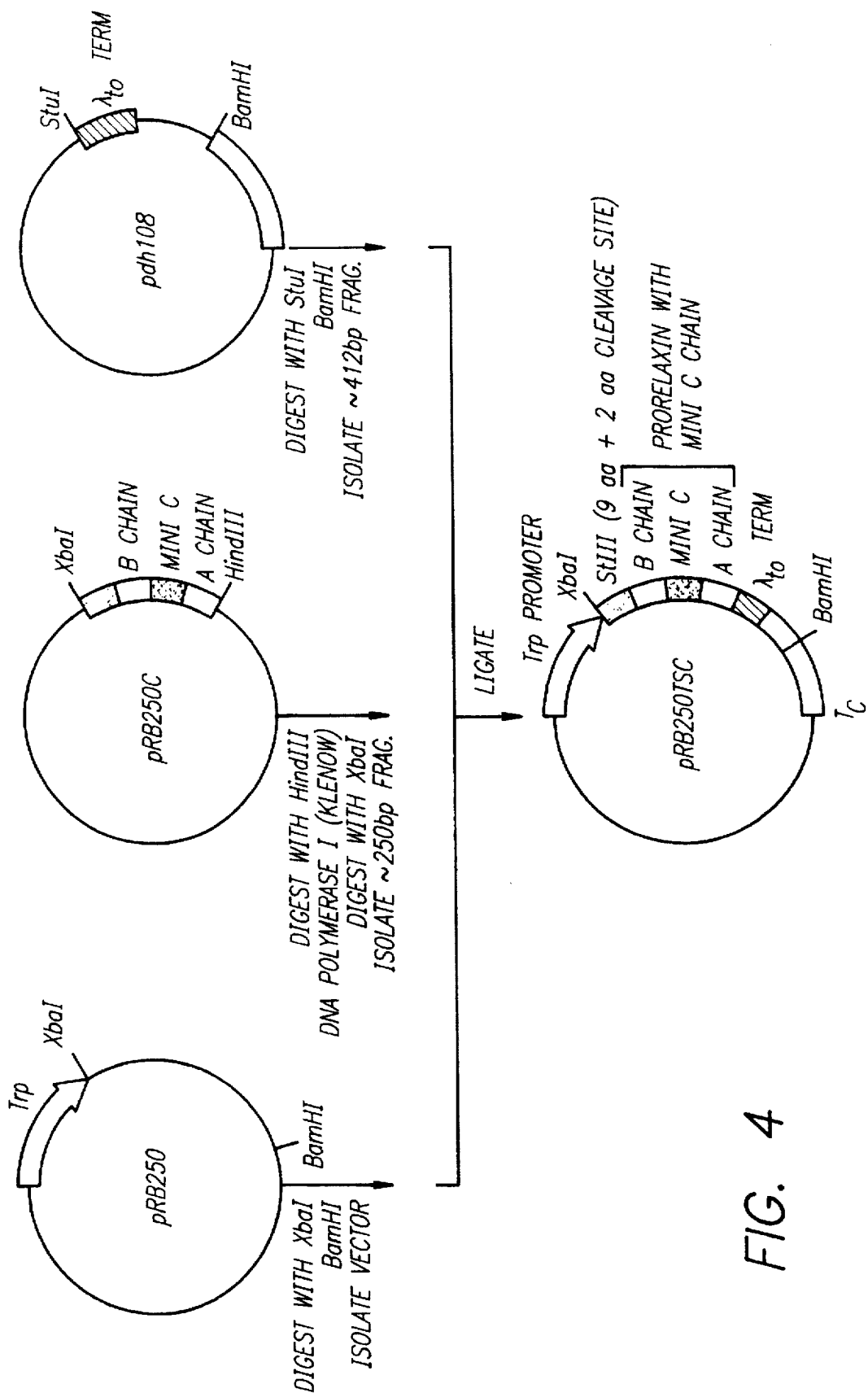
FIG. 4 illustrates the lineage of the plasmid pRB250CTsc which comprises a gene encoding a non-naturally occurring prorelaxin as depicted in FIG. 3.
Figure 5:
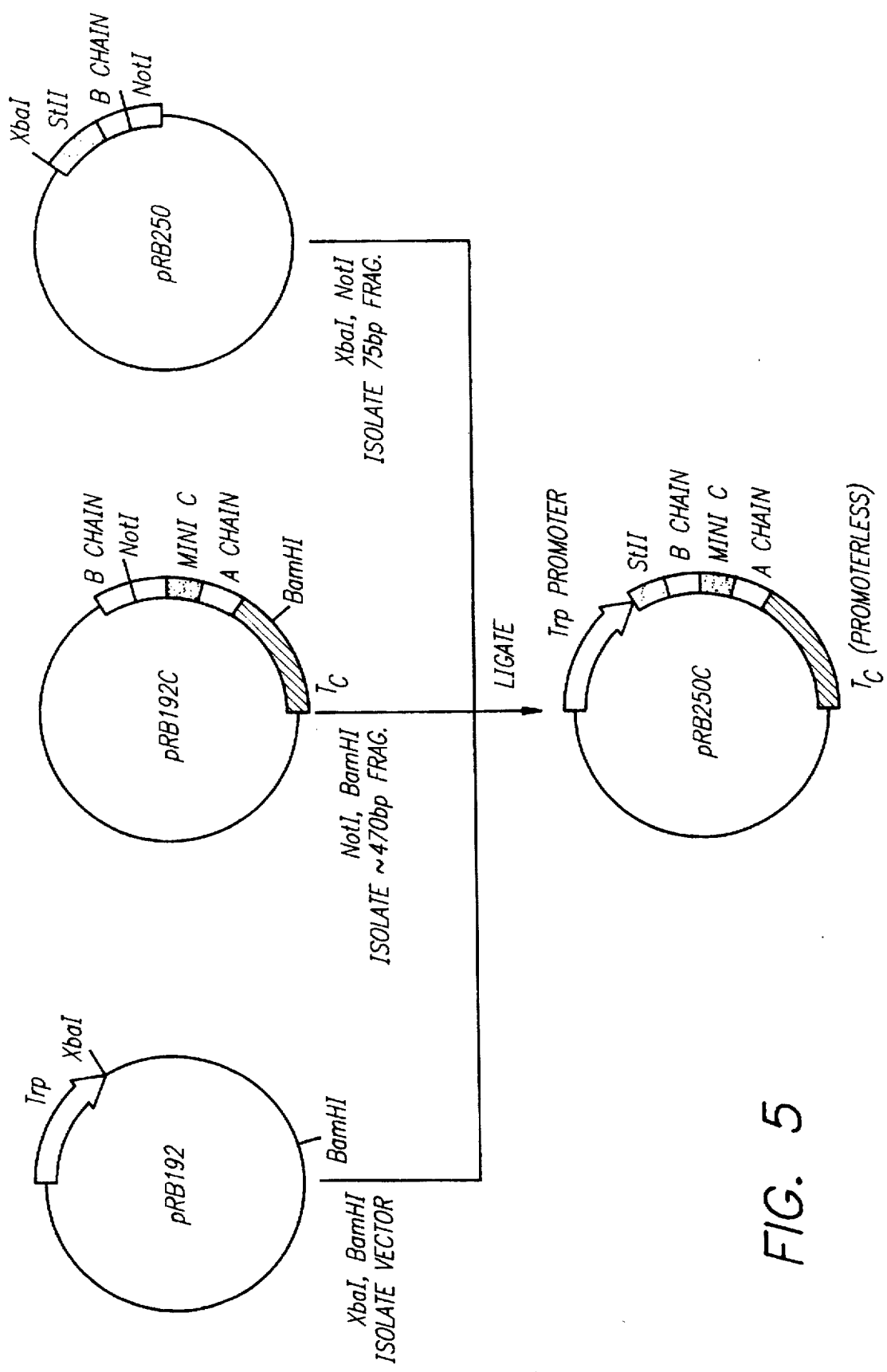
FIG. 5 illustrates the construction of plasmid pRB250C, an intermediate plasmid in the construction of pRB250CTsc.

The plasmid pRB250CTsc was constructed in several steps, as shown in FIG. 4, using as intermediate plasmids pRB250, containing the trp promoter, pRB250C, containing the non-naturally occurring prorelaxin coding sequences on a 250 base pair Xba I to Hind III fragment, and pdhlO8, containing the lambda $t_o$ transcriptional terminator on a 412 base pair Stu I to Bam HI fragment.

Plasmid pRB250

Figure 7:
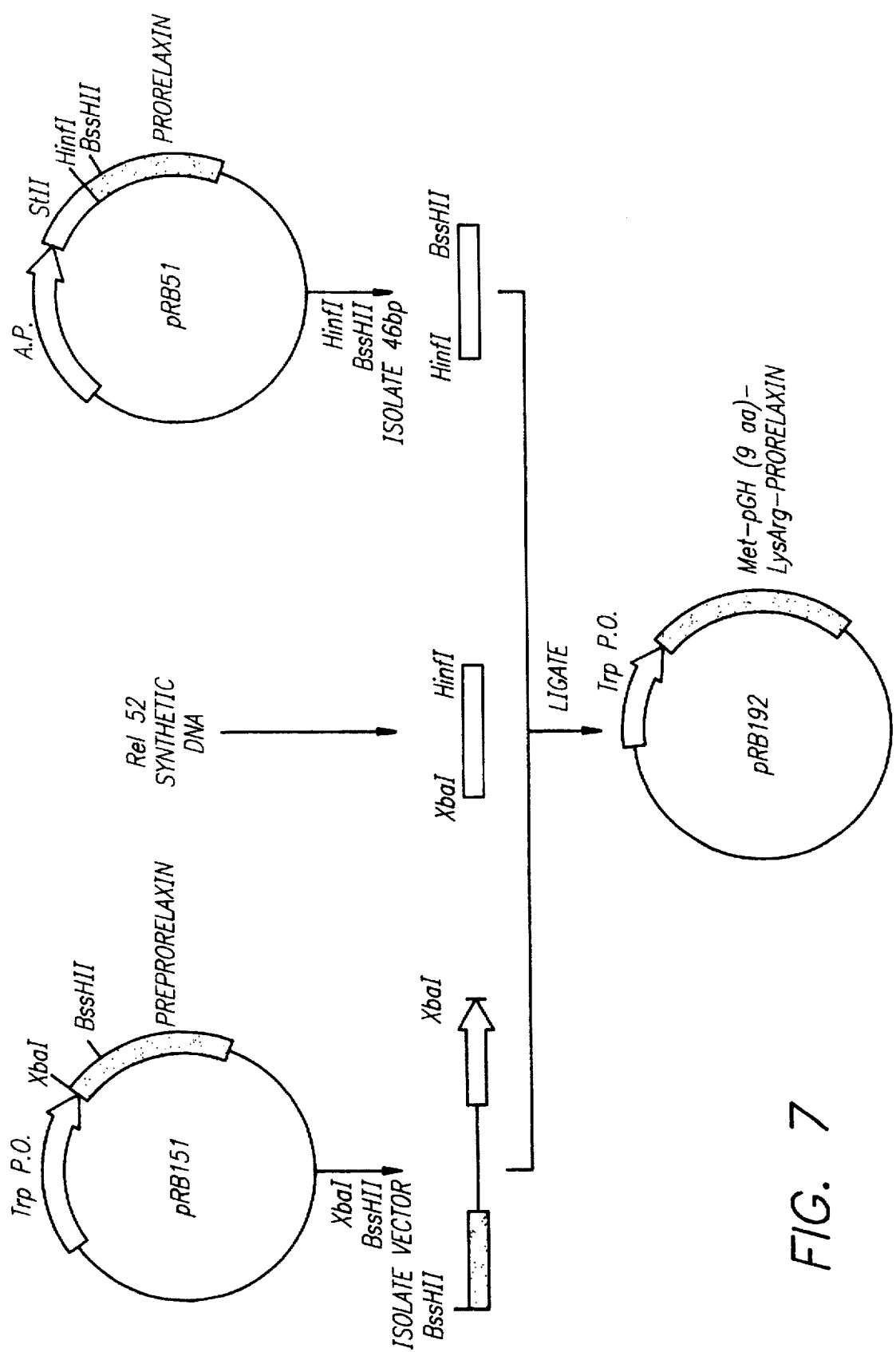
FIG. 7 illustrates the construction of plasmid pRB192, an intermediate in the construction of pRB 250.

The plasmid pRB250 results in the trp promoter/operator being ligated to 9 amino acids of the heat stable enterotoxin II (ST II) leader sequence (MKKNIAFLL) described in Picken et al., [Infect. Immun. 42, 269 (1983)] plus codons for Lys and Arg. pRB250 was prepared by ligating together three DNA fragments as shown in FIG. 7. The first of these was the vector pRB192, shown in FIG. 7, from which the small fragment from BssHII to XbaI had been removed. The second fragment is a synthetic duplex, Rel 60, encoding the STII 9 amino acids plus Lys and Arg:

```
                    MetLysLysAsnIleAlaPheLeuLeuLysArg (SEQ ID NO:1)
5'-CTAGAATTATGAAAAAGAATATCGCATTTCTTCTTAAACGGG-3' (SEQ ID NO:22)
3'-TTAATACTTTTTCTTATAGCGTAAAGAAGAATTTGCCCTGA-5' (SEQ ID NO:23)
```

The third fragment is the Hinfl to BssHII fragment from plasmid pRB51, the construction of which is described in FIG. 9.

Plasmid pRB250C

Figure 6:
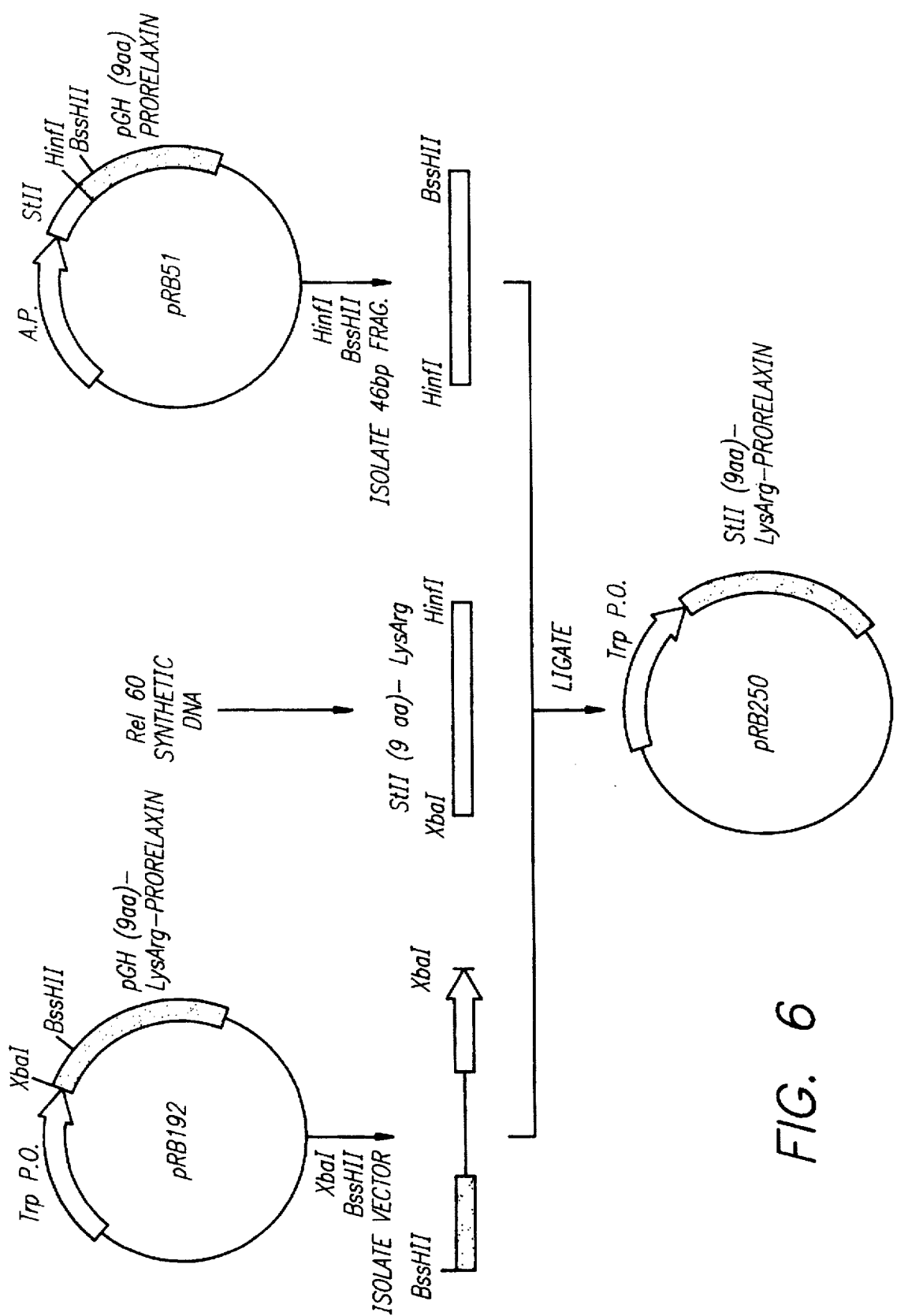
FIG. 6 illustrates the construction of plasmid pRB250, an intermediate plasmid in the construction of pRB250CTsc.

The plasmid pRB250C results in the Trp promoter being ligated to the STII leader 9 amino acids plus amino acids Lys and Arg and also contains the non-naturally occurring prorelaxin as well as a tetracycline resistance gene minus the naturally occurring tetracycline resistance gene promoter.

pRB250C was prepared by ligating together three fragments as shown in FIG. 6. The first of these was the vector pRB192 from which the small fragment from Xba I to Bam HI had been removed. The second fragment was a Not I to Bam HI fragment from pRB192C which comprised the C-peptide from the non-naturally occurring prorelaxin. The third fragment was a Not I to Xba I approximately 75 base pair fragment from pRB250.

Plasmid pdh108

Plasmid pdh108 contains the lambda transcription terminator as described in Scholtissek et al., Supra.

Plasmid pRB192

The plasmid pRB192 contains the Trp promoter ligated to amino acid methionine followed by 9 amino acids of porcine growth hormone plus Lys and Arg and also contains naturally occurring prorelaxin. pRB192 was prepared by ligating together three fragments as shown in FIG. 7. The first of these fragments was the vector pRB151 from which the small fragment Xba. I to Bss HII had been removed. The second fragment was the synthetic duplex, Rel 52, having the sequence:

MetPheProAlaMetProLeuSerSerLysArg (SEQ ID NO:26)
5'-CTAGAATTATGTTCCCAGCTATGCCTCTATCTAGTAAACGGG-3' (SEQ ID NO:24)
3'-TTAATACAAGGGTCGATACGGAGATAGATCATTTGCCCTGA-5' (SEQ ID NO:25)

which is methionine plus 9 amino acids of porcine growth hormone plus Lys and Arg. The third fragment was a Hinf I to Bss HII 46 base pair fragment from the vector pRB51.

Plasmid pRB192C

Figure 10B:
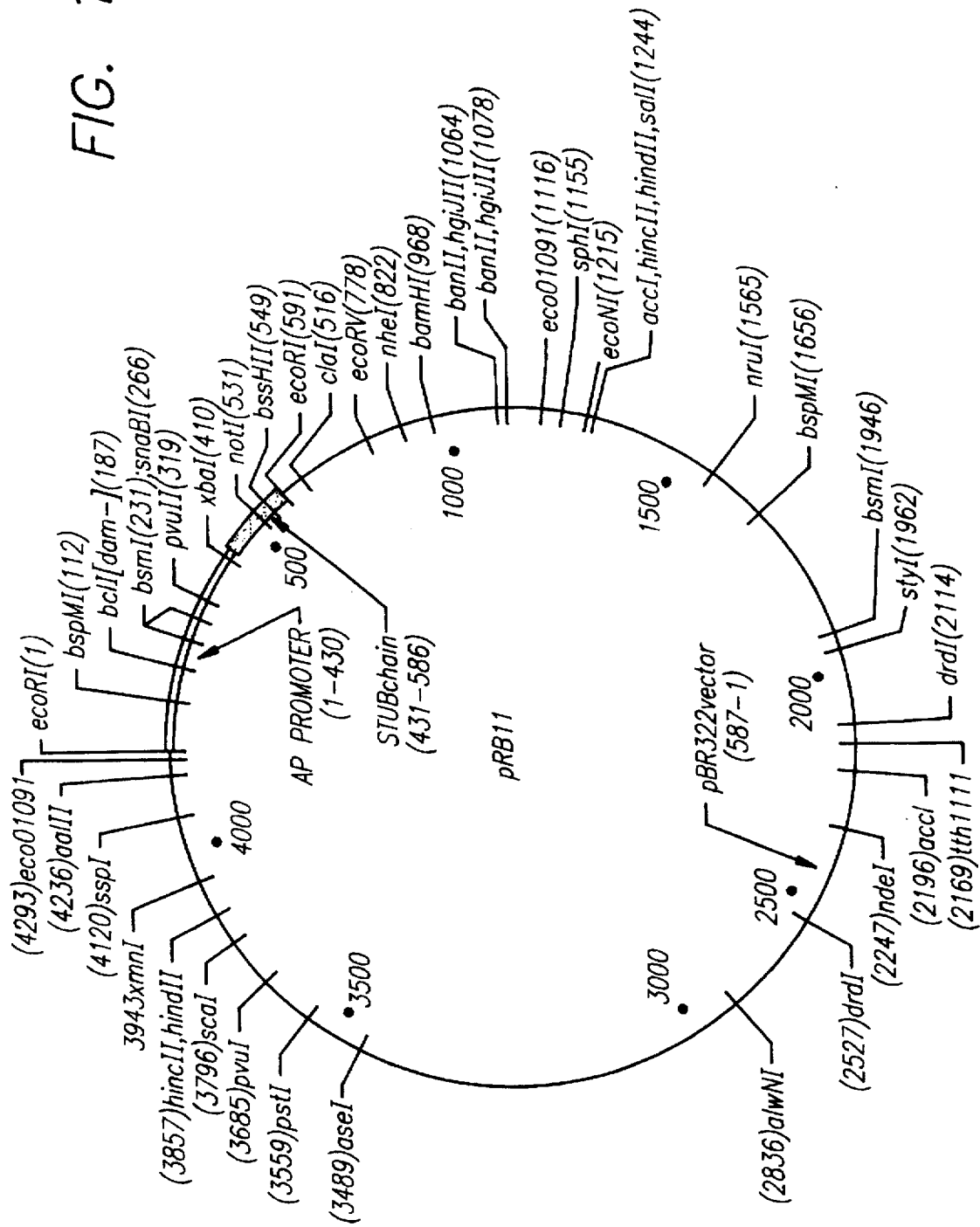
FIG. 10B illustrates the construction of pRB11.
Figure 18A:
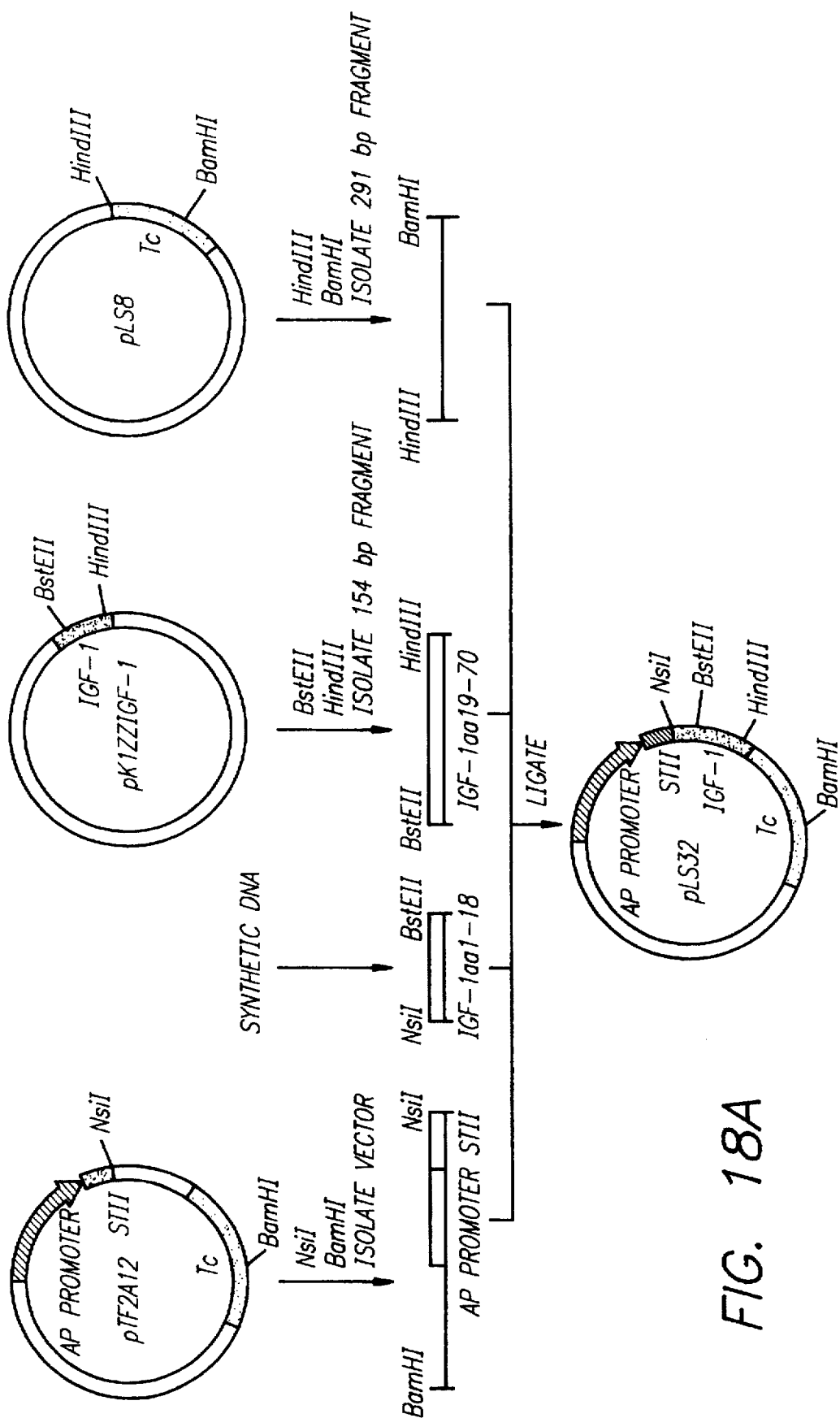
FIG. 18A illustrates the construction of pLS32, an intermediate in the construction of pLS33lamB.

Plasmid pRB192C, results in the Trp promoter being ligated to methionine followed by 9 amino acids of porcine growth hormone plus Lys and Arg and further contains non-naturally occurring prorelaxin. Plasmid pRB192C contains a promoterless tetracycline resistance gene. pRB192C was prepared by ligating together three fragments as shown in FIG. 18. The first fragment was the large vector fragment from BssHII to EcoRV from the plasmid pRB192. The second fragment was a synthetic fragment, Rel 58, containing the non-naturally occurring prorelaxin of the sequence:

has been deleted, thereby resulting in a higher plasmid copy number per cell. The coding sequence for relaxin B-chain was obtained from a preprorelaxin H2 cDNA clone [Hudson et al., *EMBO J.* 3, 2333 (1984)]. The alkaline phosphatase (AP) promoter and the heatstable enterotoxin II (STII) signal sequence is described in Chang et al., *Gene* 55, 189 [1987]. The sequence of pRB11 is shown in FIG. 10.

Plasmid pRB61

Figure 11:
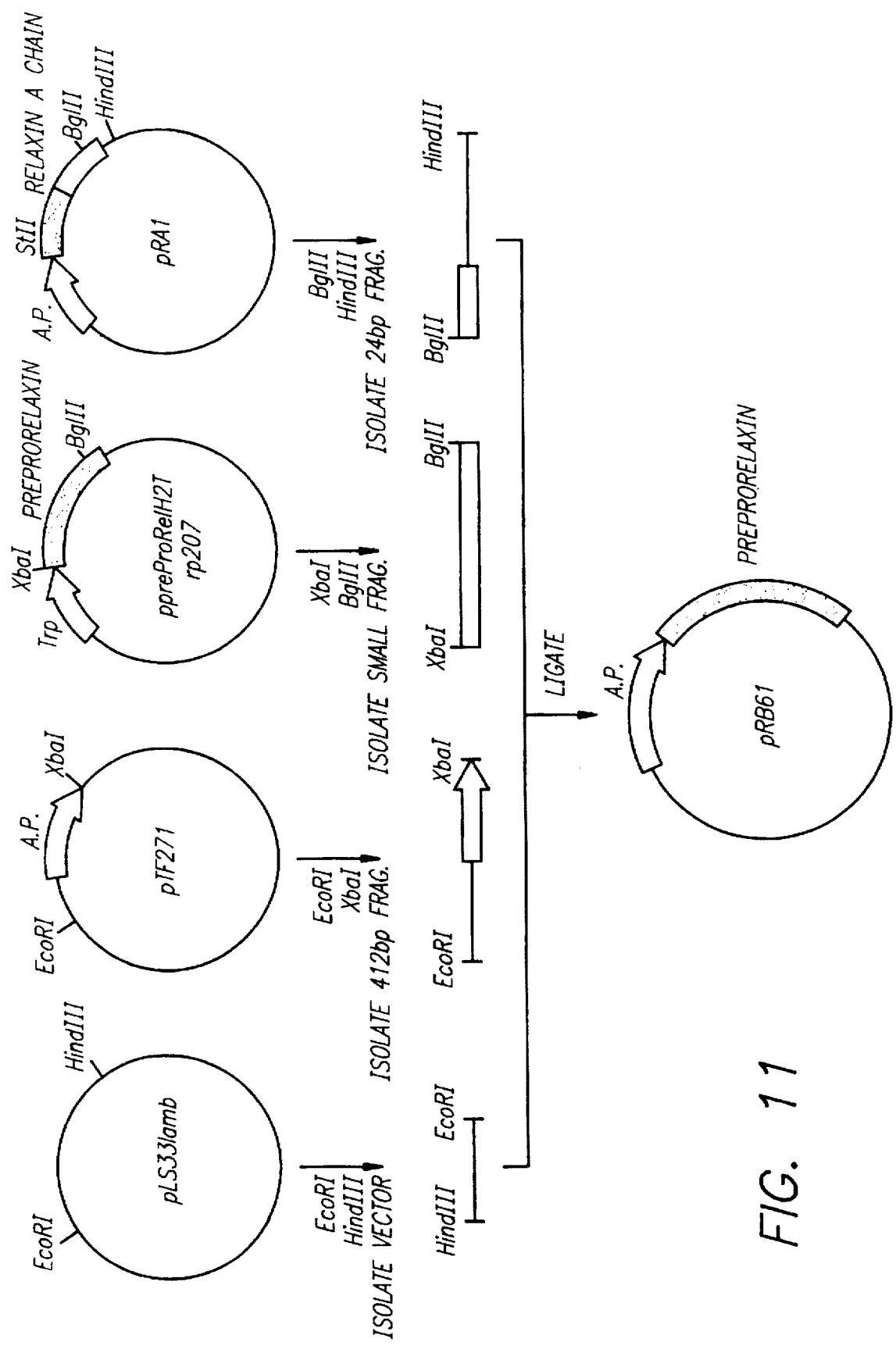
FIG. 11 illustrates the construction of plasmid pRB61, an intermediate in the construction of pRB151.
Figure 15:
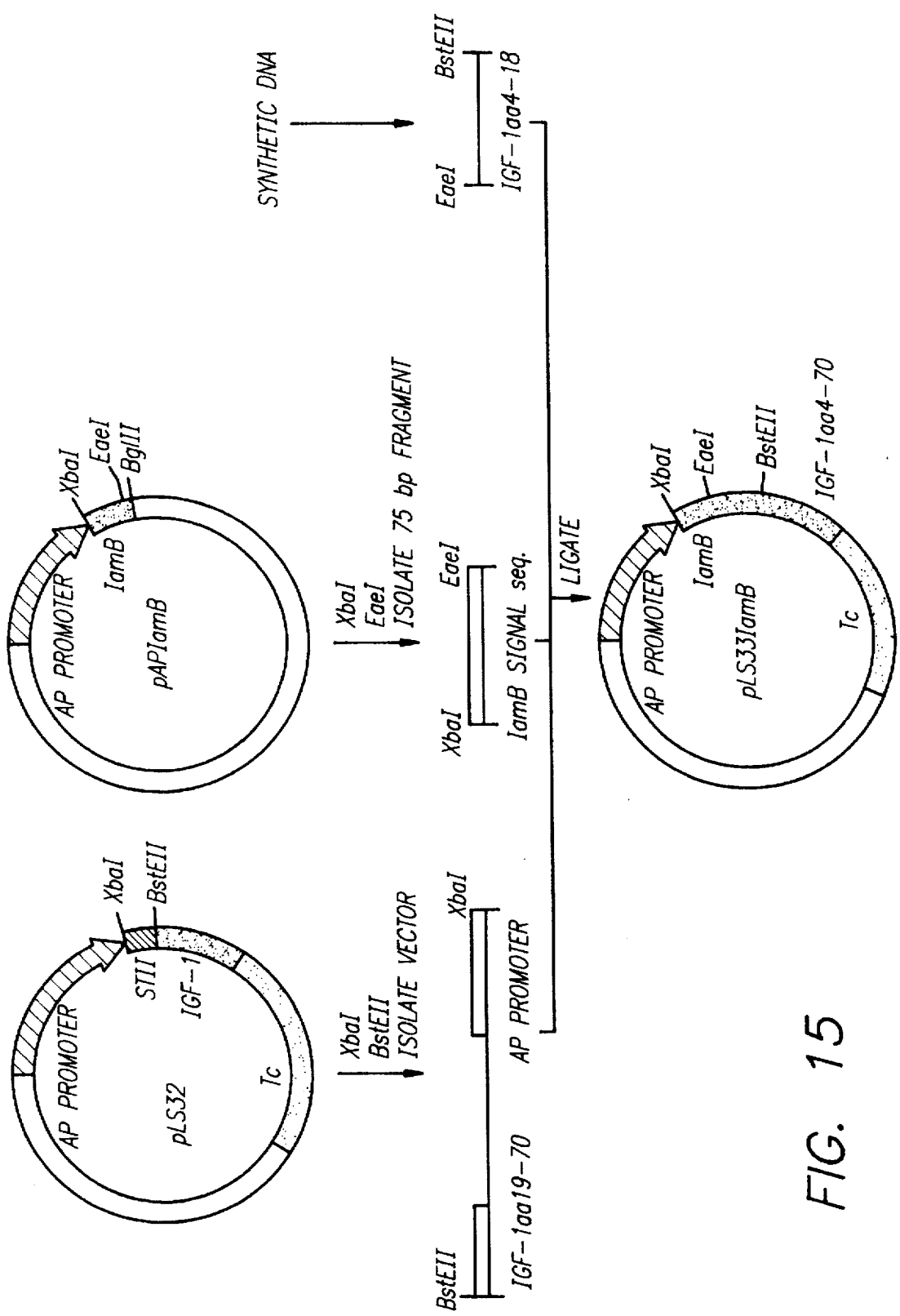
FIG. 15 illustrates the construction of pLS331amB, an intermediate in the construction of pRB61.

Plasmid pRB61 results in the alkaline phosphatase promoter being ligated to the naturally occurring preprorelaxin coding sequence. pRB61 was prepared by ligating together four fragments as shown in FIG. 11. The first fragment was an Eco RI to Hind III vector fragment from vector pLS331amB as shown in FIG. 15. The second fragment was GlnIleAlaIleCysGlyMetSerThrTrpSerLysArgLysProThrGlyTyr
5'-CGCGCAGATTGCCATTTGCGGCATGAGCACCTGGAGCAAAAGGAAACCCACTGGTTAT
3'-GTCTAACGGTAAACGCCGTACTCGTGGACCTCGTTTTCCTTTGGGTGACCAATA
GlySer (SEQ ID NO:28)
GGTTCT-3' (SEQ ID NO:27)
CCAAGAGC-5' (SEQ ID NO:29)

The third fragment was the Taq I to Eco RV 200 base pair fragment of pRB192 containing the relaxin A chain and the 5' end of the tetracycline resistance gene.

Plasmid pRB151

Figure 8:
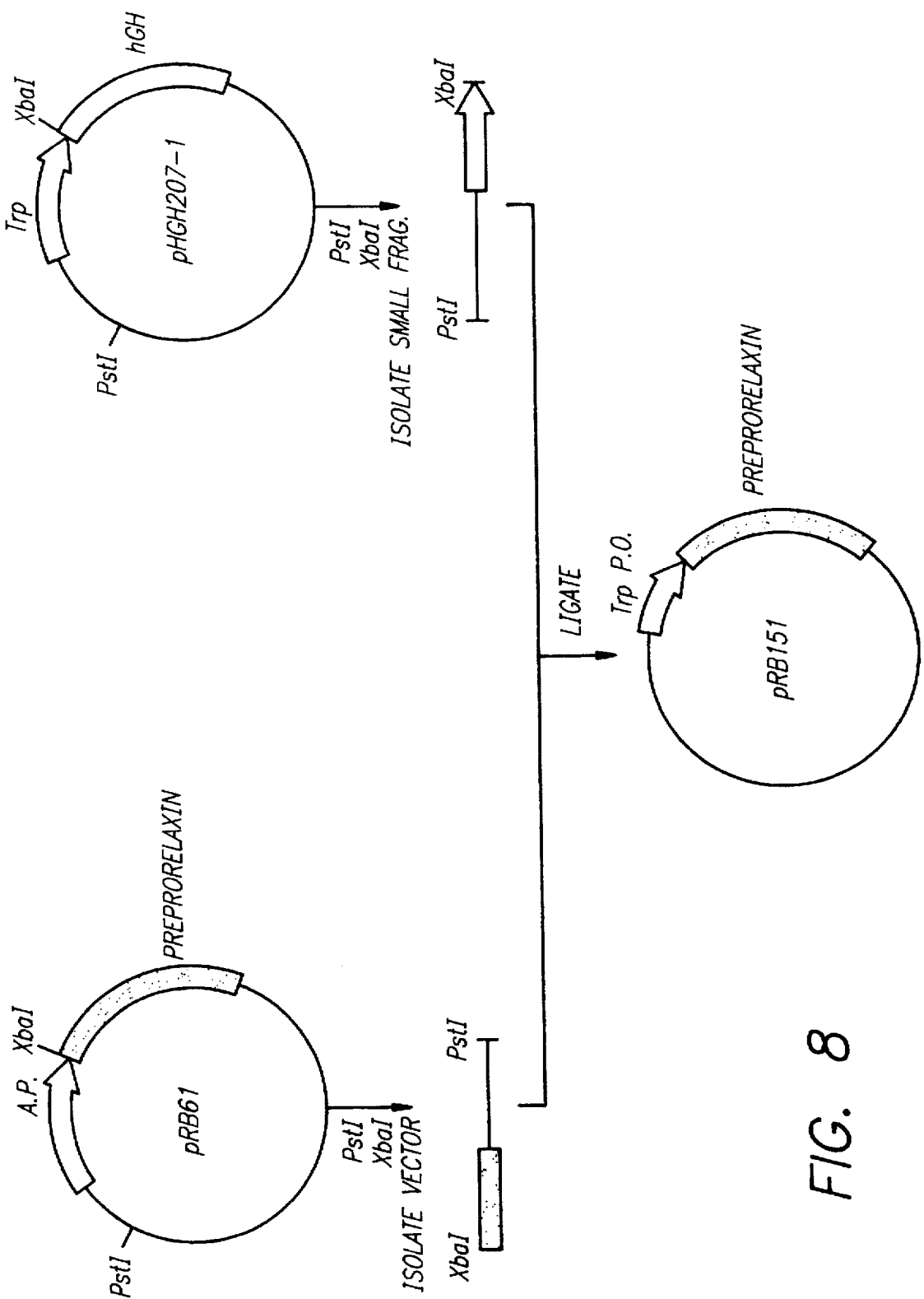
FIG. 8 illustrates the construction of plasmid pRB151, an intermediate in the construction of pRB192.

Plasmid pRB151 results in the Trp promoter being ligated to the preprorelaxin coding sequence and was prepared by ligating together two fragments as shown in FIG. 8. The first of these is a Pst I to Xba I vector fragment from plasmid pRB61. The second fragment contains the Trp promoter on a Pst I to Xba I fragment from the plasmid pHGH207-1 as described in (deBoer et al., from [*Promoters: Structure and Function*, eds. Rodriguez and Chamberlain, publisher M. J. Praeger, New York 462 (1982)].

Plasmid pRB51

Figure 9A:
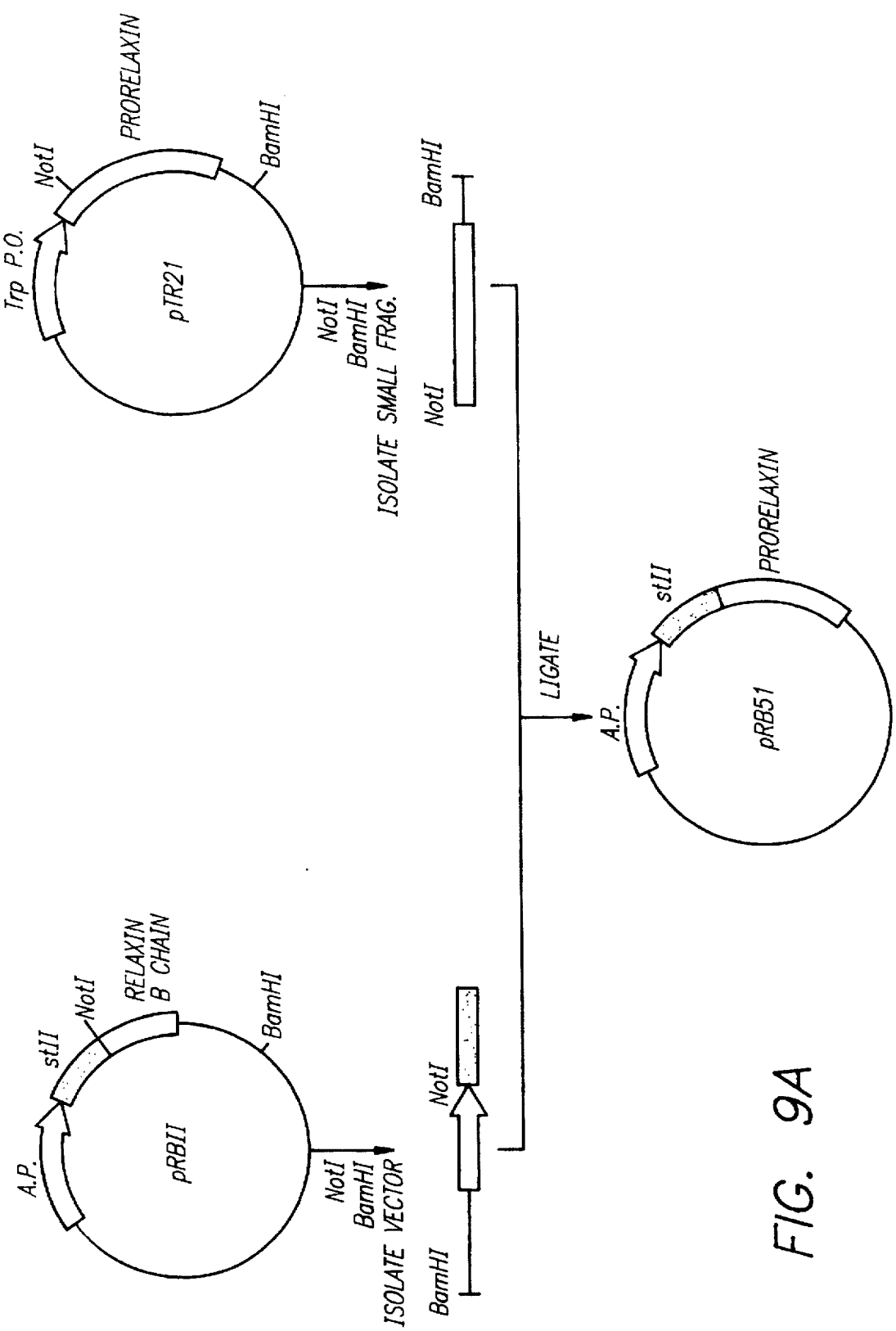
FIG. 9A illustrates the construction of plasmid pRB51, an intermediate in the construction of pRB192.
Figure 16B:
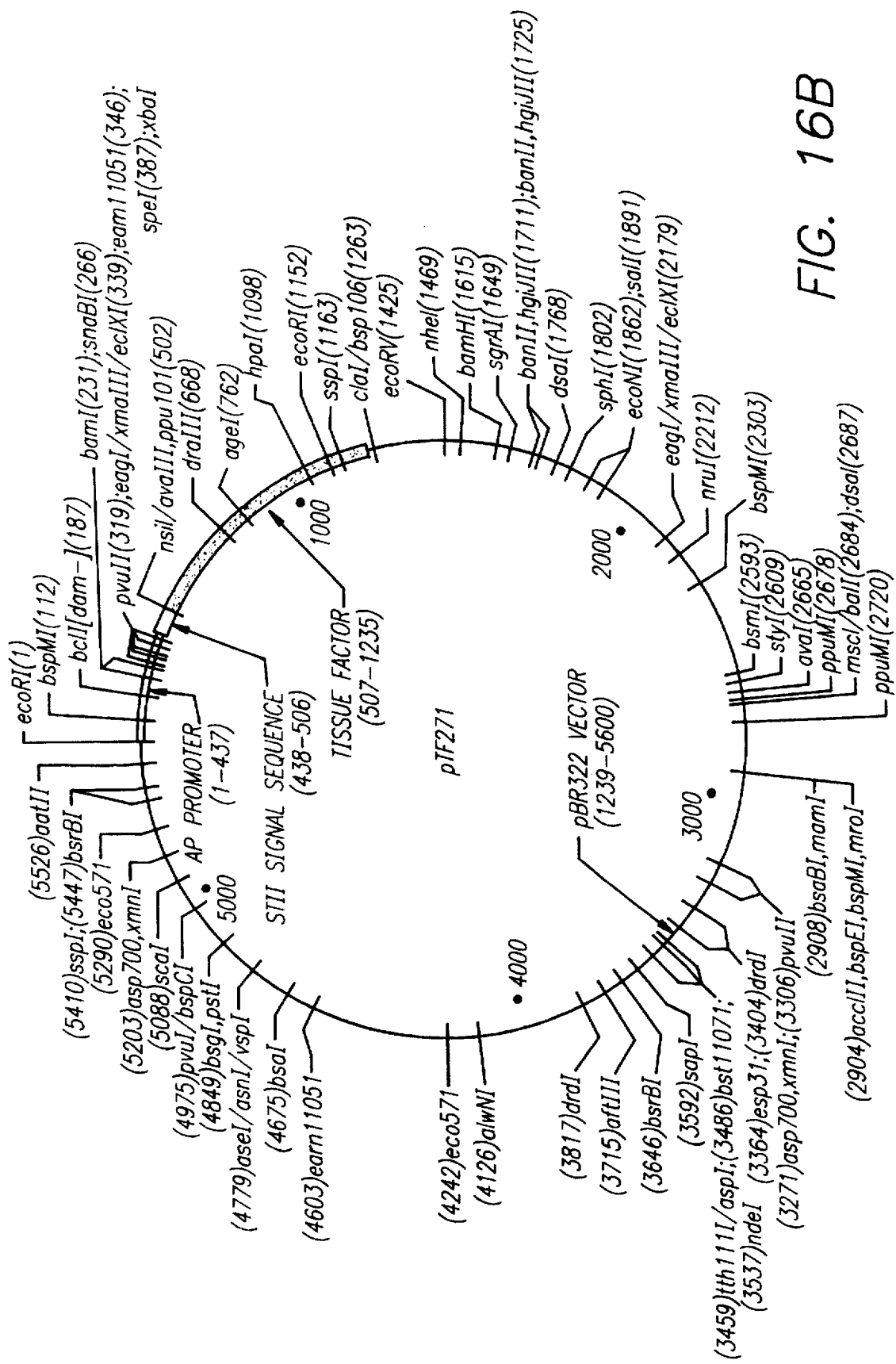
FIG. 16B illustrates the construction of pTF271.
Figure 17:
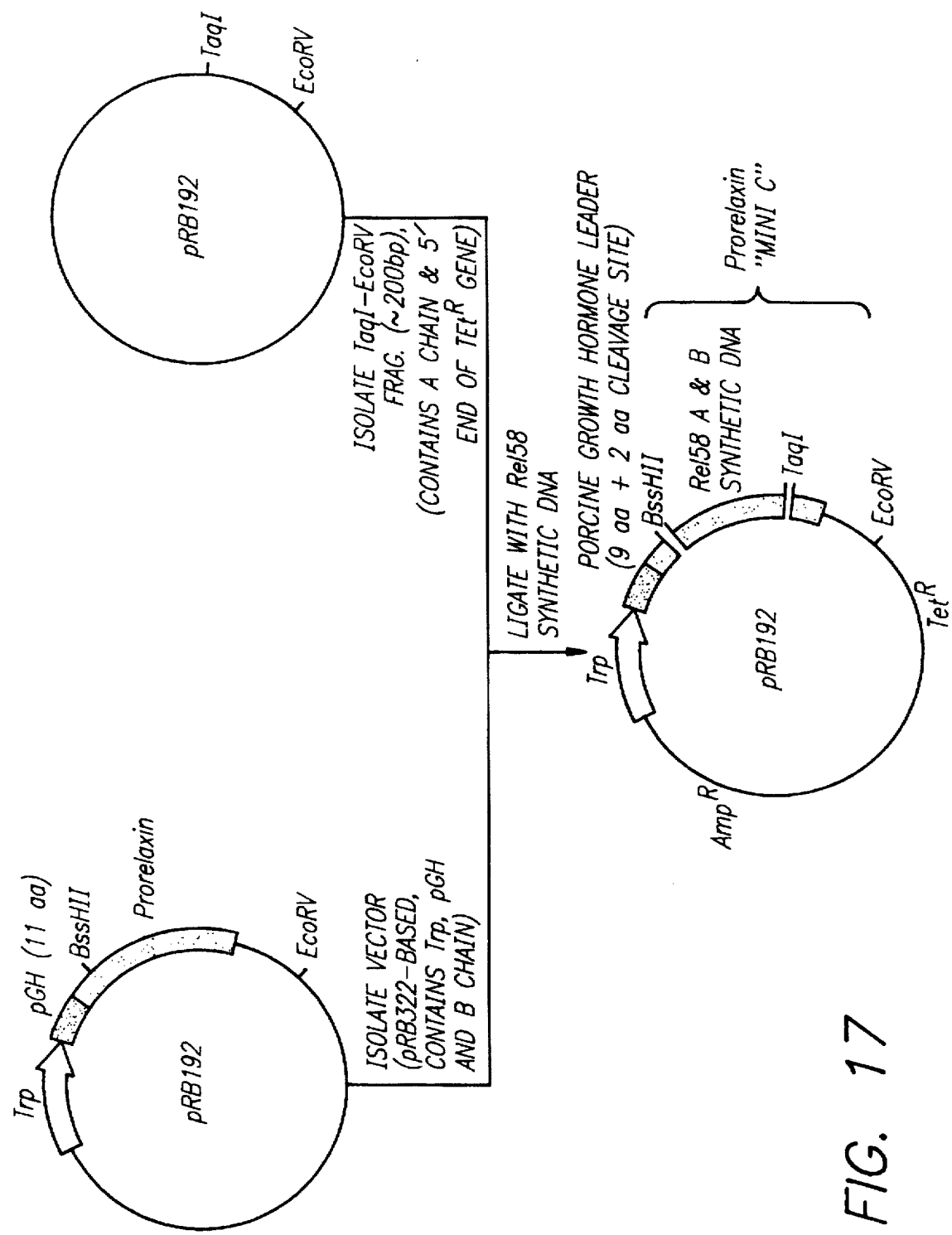
FIG. 17 illustrates the construction of pRB192C, an intermediate in the construction of pRB250C.

Plasmid pRB51 results in the alkaline phosphatase promoter being ligated to the full STII leader sequence and also contains the naturally occurring prorelaxin sequence. pRB51 was prepared by ligating together two fragments as shown in FIG. 9. The first fragment was the large vector fragment from Not I to Bam HI from plasmid pRB11; the second fragment was the small Not I to Bam HI fragment from pTR21 encoding prorelaxin amino acids 12 to 161 and whose sequence is shown in FIG. 9A. pRB11 is an expression plasmid designed to express the relaxin B-chain in *E. coli* with the aid of the STII signal sequence. The transcriptional and translational sequences required for expression are provided by the AP promoter, and the tryptophan (trp) and STII Shine-Dalgarno sequences. The plasmid origin and tetracycline resistance gene of pRB11 were derived from an altered pBR322 plasmid in which the nucleotide sequence between the AvaI and PvuII endonuclease restriction sites an Eco RI to Xba I, 412 base pair fragment from plasmid pTF271 as shown in FIG. 16. The plasmid pTF271 is designed to express the first 243 amino acids of mature human tissue factor into the periplasm of *E. coli* with the aid of the STII signal sequence. The transcriptional and translational sequences required for expression are provided by the alkaline phosphatase promoter and the trp and STII Shine-Dalgarno sequences. The coding sequence for human tissue factor is described by Fisher et al., *Throm Res* 48 89 (1987). The alkaline phosphatase promoter, tryptophan (trp) and heat stable enterotoxin II (STII) Shine-Dalgarno sequences, and the STII signal sequence were derived from phGH-1 [Chang et al., *Gene* 55 189 (1987)]. The plasmid origin and tetracycline resistance gene were derived from pBR322 [Sutcliffe *Cold Spring Harbor Symposia on Quantitative Biology* Vol. 43 77 (1978)].

The third fragment is the small Xba I to Bgl II fragment from plasmid pPreProRelH2Trp207. pPreProRelH2Trp207 is a derivative of pHGH207 (as described in U.S. Pat. No. 4,663,283 issued 5 May 1987) in which the HGH coding sequence has been replaced with that of preprorelaxin. The fourth fragment is a 24 base pair Bgl II to Hind III fragment from the vector pRA1.

Plasmid pLS331amB: pLS331amB was constructed as shown in FIG. 15 by ligating together three DNA fragments. The first of these was the vector pLS32, described below, in which the small XbaI-BstEII fragment had been removed. The second was a 75-bp XbaI-EaeI fragment from pAPlamB, described below, encoding the lamB signal sequence. The third was a 46-bp synthetic DNA duplex with the following sequence:

5'-GGCCACTCTGTGCGGTGCTGAACTGGTTGACGCTCTGCAGTTTGTTTGCG-3' (SEQ ID NO:30)
3'-TGAGACACGCCACGACTTGACCAACTGCGAGACGTCAAACAAACGCCACTG-5' (SEQ ID NO:31)

The above sequence encodes amino acids 4–18 of mature IGF-I.

pLS32 results in the fusion of the IGF-I coding sequence to that of the heat-stable enterotoxin II (STII) signal sequence and was prepared by ligating together four DNA fragments, as shown in FIG. 18. The first of these was the vector pTF2A12 [Paborsky et al., *Biochemistry* 28, 8072 (1989)] from which the small NsiI-BamHi fragment containing the tissue factor gene had been removed. The STII signal sequence is described by Picken et al., *Infect. Immun.* 42, 269 1983]. The second fragment was a 55-bp synthetic duplex encoding the first 18 amino acids of mature IGF-I. This duplex has the following sequence:

Pat. No. 4,758,516) rather than hGH and it contains a convenient BglII restriction site downstream of the promoter and ribosome binding site. The second piece in the ligation was a 80-bp synthetic DNA duplex with the following sequence, which encodes the lamB signal sequence, which has been described by Clement and Hofnung, *Cell* 27, 507 [1981]:

---

5'-CTAGAATTATGATGATTACTCTGCGCAAACTTCCTCTGGCGGTTG
3'-TTAATACTACTAATGAGACGCGTTTGAAGGAGACCGCCAAC
CCGTCGCAGCGGGCGTAATGTCTGCTCAGGCCATGGCCA-3' (SEQ ID NO:34)
GGCAGCGTCGCCCGCATTACAGACGAGTCCGGTACCGGTCTAG-5' (SEQ ID NO:35)

5'-GGTCCCGAAACTCTGTGCGGTGCTGAACTGGTTGACGCTCTGCA
3'-ACGTCCAGGGCTTTGAGACACGCCACGACTTGACCAACTGCGAGACGT
GTTTGTTTGCG-3' (SEQ ID NO:32)
CAAACAAACGCCACTG-5' (SEQ ID NO:33)

---

The third piece in the ligation was a 154 bp BstEII to HindIII fragment from pKIZZ IGF-I encoding the remaining amino acids 19–70 of IGF-I. pK1ZZIGF-I is a kanamycin-resistant plasmid containing a lac promoter attached to a Protein A promoter attached to a Protein A signal, attached to two consensus z regions from Protein A that bind IgGs and secrete proteins, fused using two codons encoding an Asn-Gly interface to a synthetic IGF-I gene and also containing an F region to five high copy number. This plasmid is similar to pZZ-IGF-I described in EP publication no. 230,869 published 5 Aug. 1987, where ampicillin gene is replaced by a kanamycin gene. The last fragment shown in FIG. 18B in the construction of pLS32 was a 291-bp HindIII-BamHI fragment from the plasmid pLS8. This last fragment is simply the coding sequence for the start of the tetracycline gene of pBR322 [Sutcliffe, *Cold Spring Harbor Symposia on Quantitative Biology* 43 77 (1978)] in which a HindIII restriction site was engineered immediately upstream of the methionine start codon.

Plasmid pAPlamB

Figure 19:
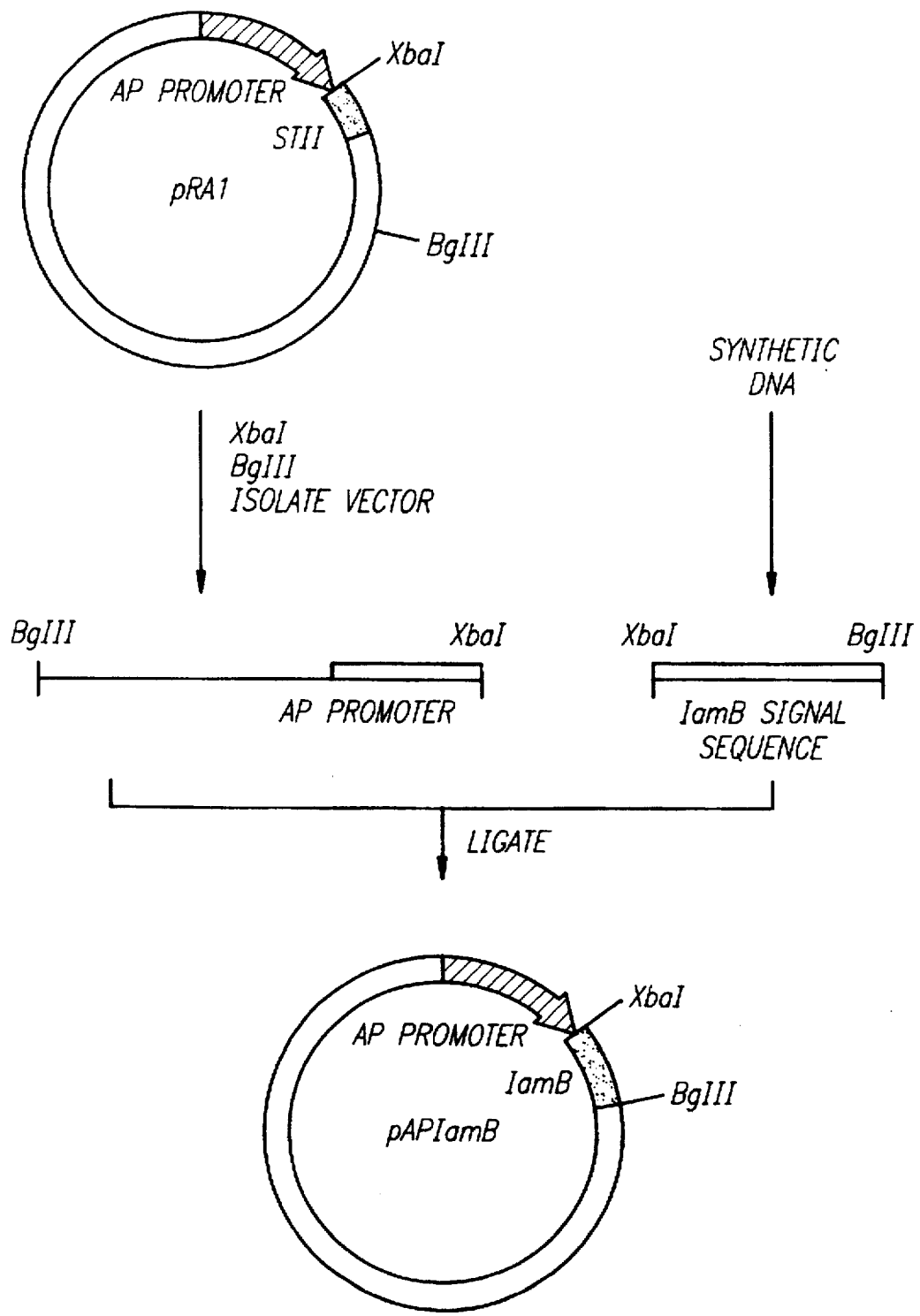
FIG. 19 illustrates the construction of' pAPlamB, an intermediate in the construction of pLS33lamB.

The plasmid pAPlamB was constructed as shown in FIG. 19, by ligating together two DNA fragments, and results in the placement of the lamB signal coding sequence downstream of the AP promoter and the trp Shine-Dalgarno sequence. Included in the ligation was the vector pRA1 in which the small XbaI-BglII fragment had been removed. This plasmid is a derivative of pHGH1 [Chang] et al., *Gene* 55, 189 (1987)), which latter plasmid contains the AP promoter, the STII signal and DNA encoding HGH. pRA1 differs from pHGH1 in that it contains DNA encoding relaxin A chain (the sequence of which is described in U.S.

Plasmid pRAL

Figure 12A:
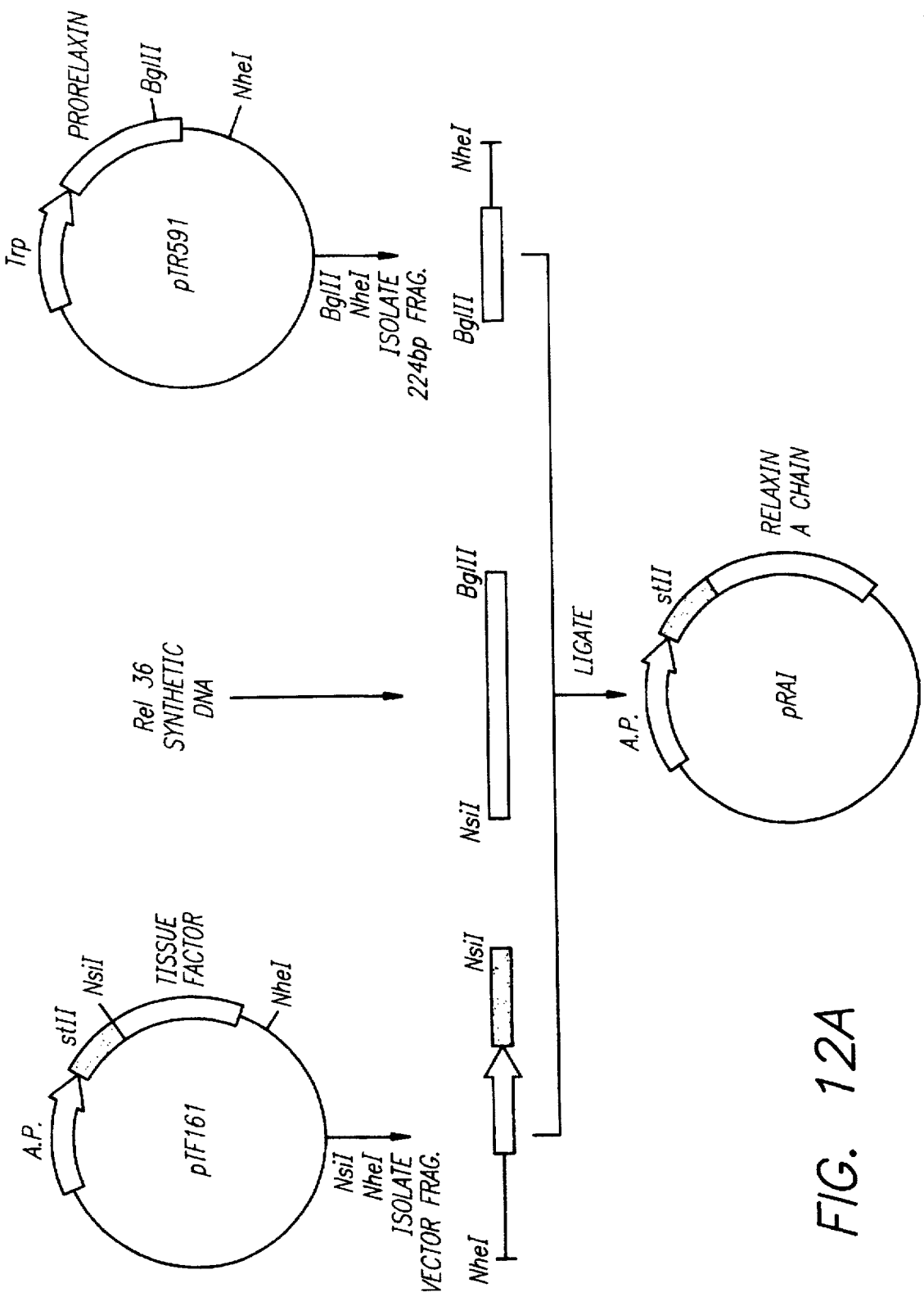
FIG. 12A illustrates the construction of plasmid pRA1, an intermediate in the construction of pRB61.
Figure 12B:
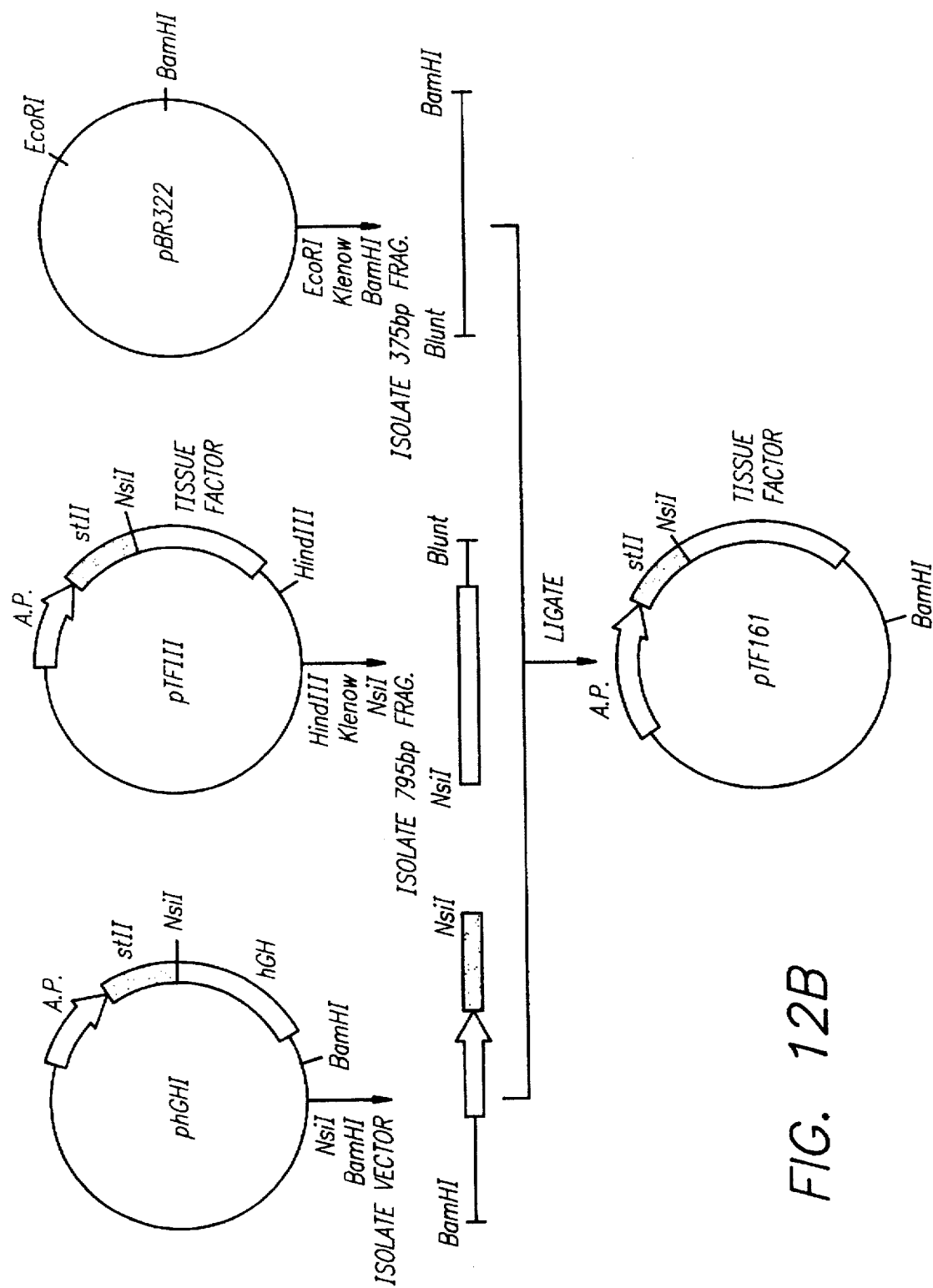
FIG. 12B illustrates the construction of PTF161.

Plasmid pRA1 results in the alkaline phosphatase promoter being fused to the STII leader sequence and further contains the coding sequence of the Relaxin A chain. pRA1 was prepared by ligating together three fragments as shown in FIG. 12. The first was a Nsi I to Nhe I large vector fragment from the plasmid pTF161, a derivative of pGH1 [Chang et al. *Gene* 55, 189 (1987)] and pTF111 [Paborsky et al., *Biochemistry* 28, 807 (1989)] as described in FIG. 12A. The second fragment is the synthetic duplex, Rel 36, having the sequence:

---

5'-CAACTCTACAGTGCATTGGCTAATAAATGTTGCCATGTTGGTTGTACC
3'-ACGTGTTGAGATGTCACGTAACCGATTATTTACAACGGTACAACCAACATGG
AAAA-3' (SEQ ID NO:36)
TTTTCTAG-5' (SEQ ID NO:37)

---

The third fragment was a 224 base pair Bgl II to Nhe I fragment from plasmid pTR591.

Plasmid pTR591

Figure 13:
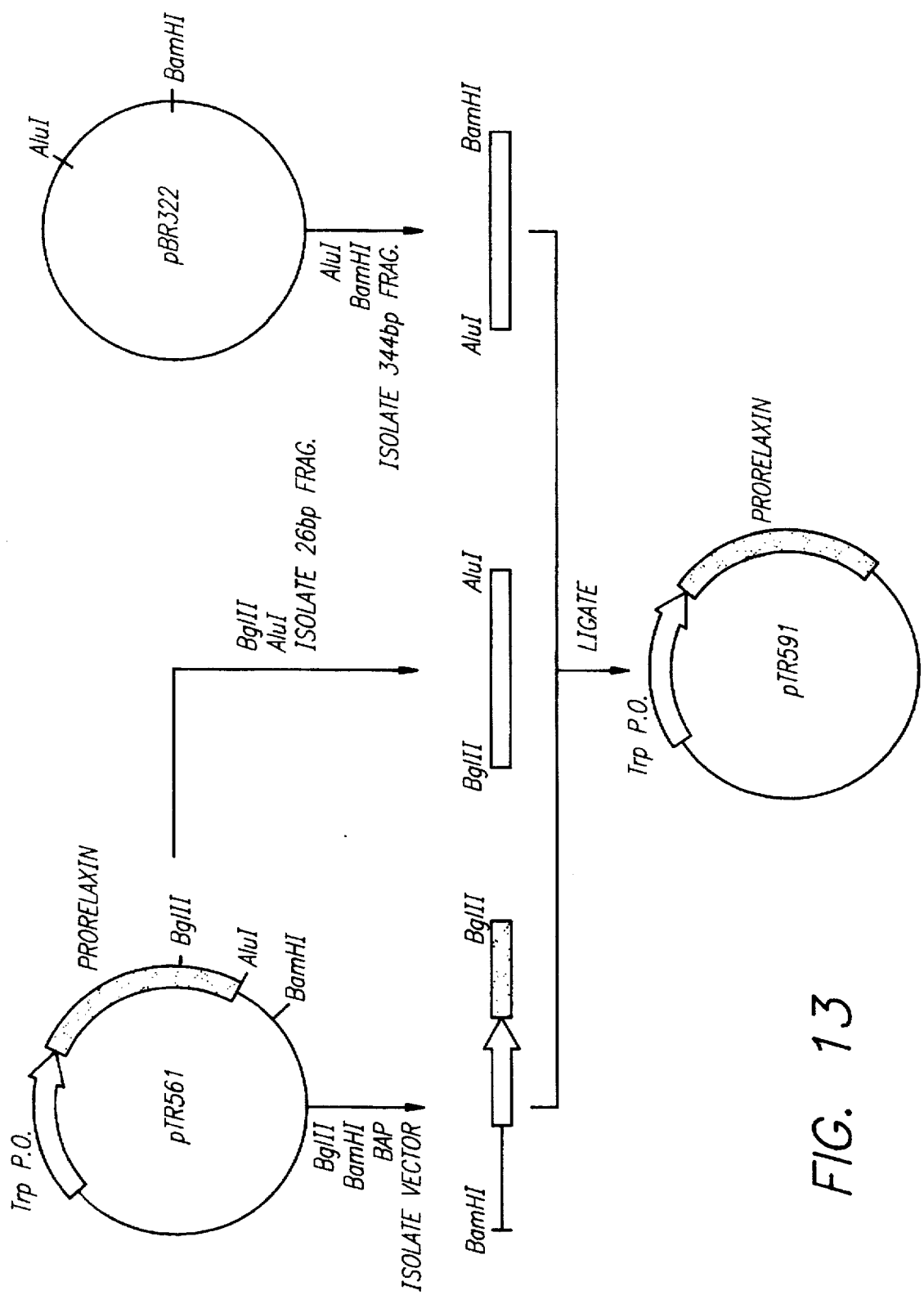
FIG. 13 illustrates the construction of pTR591, an intermediate in the construction of plasmid pRA1.
Figure 14:
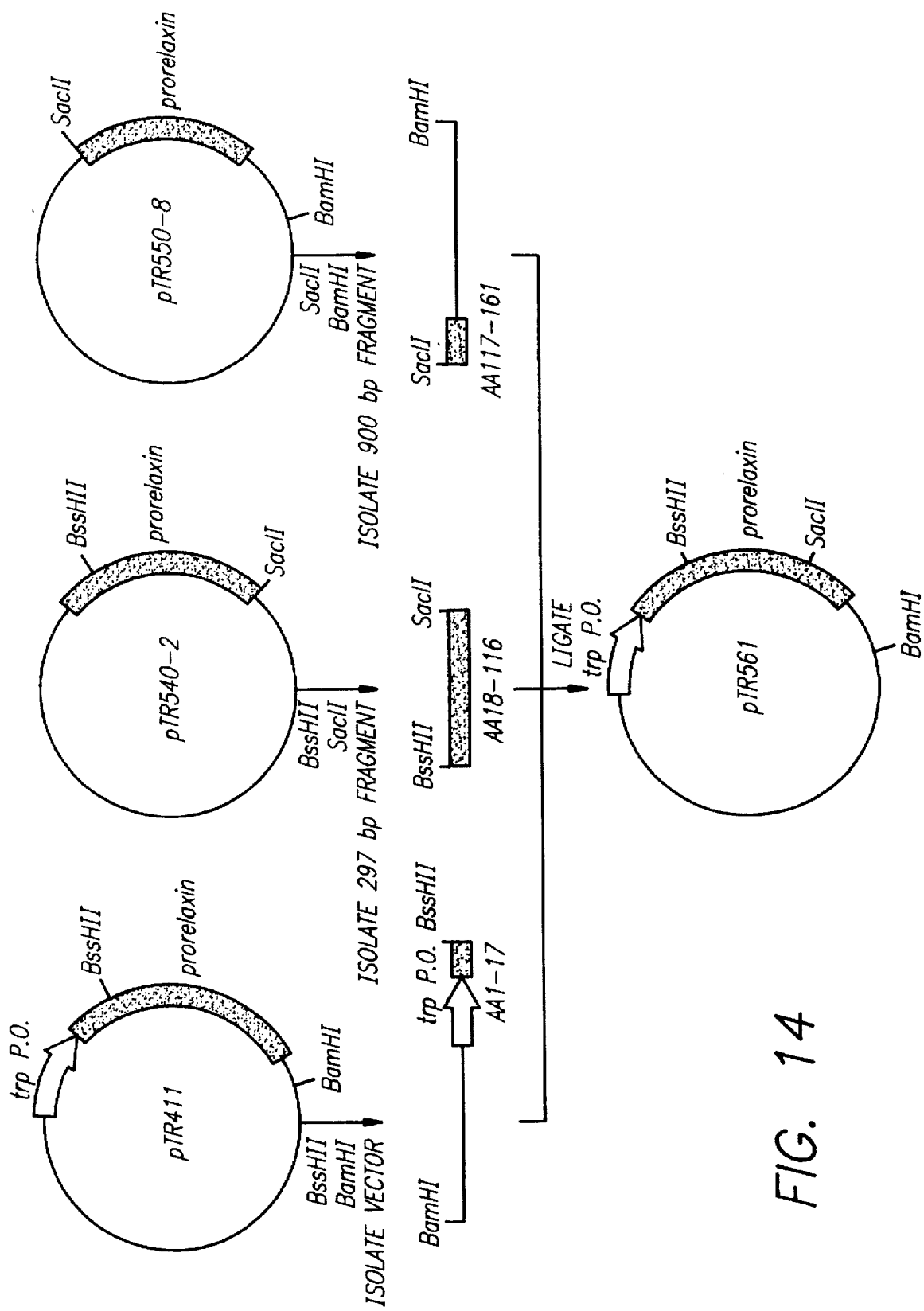
FIG. 14 illustrates the construction of pTR561, an intermediate in the construction of pTR591.

Plasmid pTR591 resulted in the trp promoter ligated to human prorelaxin. pTR591 was prepared by ligating together three fragments as shown in FIG. 13. The first fragment was the large Bgl II to Bam HI vector fragment from the plasmid pTR561 as shown in FIG. 14 and described in WO 90/13659. The second fragment was the 26 base pair Alu I to Bgl II fragment from pTR561, while the third fragment was a 344 base pair Alu I to Bam HI fragment from pBR322.

In addition to the plasmid pRB25OCTsc, other plasmids comprised of prorelaxin having non-naturally occurring leader and C-peptides were constructed as shown in FIG. 2.

EXAMPLES 2 to 4

The prorelaxin expression vectors, pRELCIII, pRELCAspN, and pRELCLysC, comprised of non-naturally occurring leader-C-peptides having enzymatic cleavage sites (See FIG. 2) are constructed as above for pRB250CTsc with appropriate substitution of synthetic C-peptide coding sequences.

EXAMPLE 5
A process for producing relaxin from a non-naturally occurring prorelaxin using trypsin and CPB Fermentation and initial isolation of the refractile bodies:

W3110tonA transfected with pRB250CTsc is used in fermentation. An LB shake flask grown at 37° C. for about 8 hours is used to inoculate at 60 L seed fermentation. The 60 L culture is grown at 37° C. to an OD550 of 45±5 (approximately 8–9 hours), then used to inoculate a 1000 L production fermentation. The 1000 L culture is grown at 37° C. and harvested 8 hours after the addition of Indoleacetic Acetic Acid (IAA), usually 12–16 hours after the time of inoculation. The medium employed is LB Flask–Luria broth+5 micrograms tetracycline/mL.

The harvested cells are then treated with the process steps outlined below.

At harvest time the cells are killed by passing the broth through a heat-kill apparatus. The mixture is cooled to 2–8C. EDTA is added to a final concentration of 5 mM and the pH is adjusted to 5.5. The cells are broken, (e.g., in Gaulin homogenizer) and the refractile bodies are collected by centrifugation (e.g. Alfa Laval AX213). The pelleted refractile bodies are frozen and stored at about −70° C.

Extraction, folding and purification of mini-C prorelaxin

The frozen refractile bodies are solubilized in 14 L to 20 L of extraction buffer (3.5M guanidine hydrochloride/5 mM Tris/0.2% EDTA, pH 8.5) per kg of refractile bodies.

The prorelaxin is refolded by diluting the above extract with 50 mM Tris/0.2% EDTA, pH 8.5 to a final volume of 60 L per kg of refractile bodies. Cystamine (0.113 g/L) and cysteine (0.606 g/L) are added and the mixture stirred for about an hour to allow folding of the prorelaxin. After completion of the refolding polyethyleneimine is added to a final concentration of about 0.05 to 0.1%. The resulting suspension is stirred gently for about an hour. After an additional dilution to 120l?kg with 50 mM Tris/0.2% EDTA, pH 8.5 the suspension is stirred gently for an additional hour.

The solids are removed by centrifugation (e.g. CEPA Z101 or Alfa Laval AX 213) and the resulting supernatant is filtered through a depth filter (e.g. CUNO). The clear solution is loaded onto a silica column equilibrated in 3.5M urea/50 mM Tris/0.2% EDTA, pH 8.5. After the column is washed with 5M urea/50 mM Tris/0.2% EDTA, pH 8.5, the folded prorelaxin is eluted with 5M urea/5 mM Tris/0.2% EDTA/0.5M TMAMC, pH 8.5.

The resulting pool is further purified by cation exchange chromatography (e.g. S-Sepharose Fast Flow). The solution is directly applied to the column equilibrated in 3.5M Urea/5 mM Tris/0.2% EDTA, pH 8.5. The column is washed with the same buffer. The prorelaxin is eluted with the same buffer containing 0.5M NaCl.

Enzymatic cleavage of mini-C prorelaxin

The pool from the ion exchange column is concentrated to about 5–10 mg/mL and diafiltered into 50 mM Tris/5 mM Cacl2 pH 8.5 on a 5K cutoff membrane (e.g. Filtron PES Omega).

Trypsin is added to the solution at a 1:100 w/w ratio (e.g. 1 MG trypsin per 100 mg of prorelaxin). After 30 minutes Carboxypeptidase B is added to the mixture (0.2rEU of CPB per mg of prorelaxin). The progress of the cleavage reaction is followed by analytical reversed phase chromatography on a C4 or C18 column. After completion the reaction is stopped by the addition of glacial acetic acid (3 mL per liter of reaction mixture).

Cyclization of the N-terminal glutamine of the A-chain

The acidified solution is heated to about 85C, held there for about an hour and then cooled down to about 10C. The resulting suspension is diluted by the addition of an equal volume of 0.5M acetic acid and centrifuged. The pellet can be washed with 0.5M acetic acid and recentrifuged. The resulting supernatants are combined and filtered.

Purification of relaxin

The clear supernatants are loaded onto a cation exchange column (e.g. S-Sepharose high performance) equilibrated in 0.5M acetic acid/50 mM Tris/5 mMCaCl2, pH 3.5. After completion of the loading the column is first washed with the equilibration buffer, then with 50 mM MES, pH 7.0 and 50 mM MES/125 mM NaCl, pH 7.0. The relaxin is eluted with a gradient of NaCl from 125 mM to 140 mM in 50 mM MES at pH 7.0.

Reversed phase chromatography is performed on a C4 or C18 silica column equilibrated in 0.1% phosphoric acid. Relaxin is eluted with a gradient of the equilibration buffer and 0.1% phosphoric acid/80% acetonitrile.

The resulting pool is directly loaded onto a high performance cation exchange column (e.g. MONO S) equilibrated in 20 mM MES/5% ethanol, pH 6.0 Relaxin is eluted with a gradient of NaCl from 10 mM to 32 mM in 20 mM MES/5% ethanol, pH 6.0.

The relaxin is then formulated by size exclusion chromatography (e.g., Sephadex G-15) or by ultra- and difiltration on a 5K cutoff membrane (e.g., Amicon YM-5, Filtron Omega) with either 10 mM citrate/isotonic saline, pH 5.0 or 20 mM sodium acetate, pH 50.

Concluding Remarks

The foregoing description details specific methods that can be employed to practice the present invention. Having detailed specific methods initially used to characterize, prepare and use the particular compounds hereof, and further disclosure as to the specific model systems employed, those skilled in the art will well enough know how to devise alternative reliable methods for arriving at the same information and for extending this information to other compounds and systems. Thus, however detailed the foregoing may appear in text, it should not be construed as limiting the overall scope hereof; rather, the ambit of the present invention is to be governed only by the lawful construction of the appended claims.

---

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Met  Lys  Lys  Asn  Ile  Ala  Phe  Leu  Leu  Lys  Arg
 1              5                        10
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

```
Asp  Ser  Trp  Met  Glu  Glu  Val  Ile  Lys  Leu  Cys  Gly  Arg  Glu  Leu  Val
 1                  5                        10                       15

Arg  Ala  Gln  Ile  Ala  Ile  Cys  Gly  Met  Ser  Thr  Trp  Ser
                20                       25
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
Lys  Arg  Lys  Pro  Thr  Gly  Tyr  Gly  Ser  Arg  Lys  Lys  Arg
 1                  5                        10
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

```
Gln  Leu  Tyr  Ser  Ala  Leu  Ala  Asn  Lys  Cys  Cys  His  Val  Gly  Cys  Thr
 1                  5                        10                       15

Lys  Arg  Ser  Leu  Ala  Arg  Phe  Cys
                20
```

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

Lys Arg Lys Pro Thr Gly Tyr Gly Ser Arg Lys Lys Arg
1               5                       10

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

Asp Lys Lys Arg Thr Gly Tyr Gly Ser Arg Arg Arg Lys
1               5                       10

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

Asp Lys Lys Arg Thr Gly Tyr Gly Ser Arg Lys Lys Arg
1               5                       10

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

Lys Arg Lys Pro Thr Gly Tyr Gly Ser Arg Arg Arg Lys
1               5                       10

( 2 ) INFORMATION FOR SEQ ID NO:9:

( i ) SEQUENCE CHARACTERISTICS:
        ( A ) LENGTH: 231 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 1..231

( x i ) SEQUENCE DESCRIPTION: SEQ ID NO:9:

```
ATG  AAA  AAG  AAT  ATC  GCA  TTT  CTT  CTT  AAA  CGG  GAC  TCA  TGG  ATG  GAG      48
Met  Lys  Lys  Asn  Ile  Ala  Phe  Leu  Leu  Lys  Arg  Asp  Ser  Trp  Met  Glu
 1              5                        10                       15

GAA  GTT  ATT  AAA  TTA  TGC  GGC  CGC  GAA  TTA  GTT  CGC  GCG  CAG  ATT  GCC      96
Glu  Val  Ile  Lys  Leu  Cys  Gly  Arg  Glu  Leu  Val  Arg  Ala  Gln  Ile  Ala
                20                       25                       30

ATT  TGC  GGC  ATG  AGC  ACC  TGG  AGC  AAA  AGG  AAA  CCC  ACT  GGT  TAT  GGT     144
Ile  Cys  Gly  Met  Ser  Thr  Trp  Ser  Lys  Arg  Lys  Pro  Thr  Gly  Tyr  Gly
```

```
                          35                       40                            45
TCT GGA AAA AAG AGA CAA CTC TAC AGT GCA TTG GCT AAT AAA TGT TGC        192
Ser Gly Lys Lys Arg Gln Leu Tyr Ser Ala Leu Ala Asn Lys Cys Cys
         50                       55                       60

CAT GTT GGT TGT ACC AAA AGA TCT CTT GCT AGA TTT TGC                    231
His Val Gly Cys Thr Lys Arg Ser Leu Ala Arg Phe Cys
 65                  70                       75
```

( 2 ) INFORMATION FOR SEQ ID NO:10:

( i ) SEQUENCE CHARACTERISTICS:
        ( A ) LENGTH: 77 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Lys Lys Asn Ile Ala Phe Leu Leu Lys Arg Asp Ser Trp Met Glu
 1               5                   10                      15

Glu Val Ile Lys Leu Cys Gly Arg Glu Leu Val Arg Ala Gln Ile Ala
             20                  25                  30

Ile Cys Gly Met Ser Thr Trp Ser Lys Arg Lys Pro Thr Gly Tyr Gly
             35                  40                  45

Ser Gly Lys Lys Arg Gln Leu Tyr Ser Ala Leu Ala Asn Lys Cys Cys
         50                  55                  60

His Val Gly Cys Thr Lys Arg Ser Leu Ala Arg Phe Cys
 65                  70                  75
```

( 2 ) INFORMATION FOR SEQ ID NO:11:

( i ) SEQUENCE CHARACTERISTICS:
        ( A ) LENGTH: 915 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 3..452

( x i ) SEQUENCE DESCRIPTION: SEQ ID NO:11:

```
GC GGC CGC GAA TTA GTT CGC GCG CAG ATT GCC ATT TGC GGC ATG AGC         47
   Gly Arg Glu Leu Val Arg Ala Gln Ile Ala Ile Cys Gly Met Ser
    1               5                   10                  15

ACC TGG AGC AAA AGG TCT CTG AGC CAG GAA GAT GCT CCT CAG ACA CCT        95
Thr Trp Ser Lys Arg Ser Leu Ser Gln Glu Asp Ala Pro Gln Thr Pro
                 20                  25                  30

AGA CCA GTG GCA GAA ATT GTG CCA TCC TTC ATC AAC AAA GAT ACA GAA       143
Arg Pro Val Ala Glu Ile Val Pro Ser Phe Ile Asn Lys Asp Thr Glu
                 35                  40                  45

ACC ATA AAT ATG ATG TCA GAA TTT GTT GCT AAT TTG CCA CAG GAG CTG       191
Thr Ile Asn Met Met Ser Glu Phe Val Ala Asn Leu Pro Gln Glu Leu
         50                  55                  60

AAG TTA ACC CTG TCT GAG ATG CAG CCA GCA TTA CCA CAG CTA CAA CAA       239
Lys Leu Thr Leu Ser Glu Met Gln Pro Ala Leu Pro Gln Leu Gln Gln
 65                  70                  75

CAT GTA CCT GTA TTA AAA GAT TCC AGT CTT CTC TTT GAA GAA TTT AAG       287
His Val Pro Val Leu Lys Asp Ser Ser Leu Leu Phe Glu Glu Phe Lys
 80                  85                  90                  95

AAA CTT ATT CGC AAT AGA CAA AGT GAA GCC GCA GAC AGC AGT CCT TCA       335
Lys Leu Ile Arg Asn Arg Gln Ser Glu Ala Ala Asp Ser Ser Pro Ser
```

|  |  |  |  |  |  |  |  |  |  |  |  |  |  |  |  |
|---|---|---|---|---|---|---|---|---|---|---|---|---|---|---|---|
|  |  |  |  | 100 |  |  |  |  | 105 |  |  |  |  | 110 |  |
| GAA | TTA | AAA | TAC | TTA | GGC | TTG | GAT | ACT | CAT | TCT | CGA | AAA | AAG | AGA | CAA | 383
| Glu | Leu | Lys | Tyr | Leu | Gly | Leu | Asp | Thr | His | Ser | Arg | Lys | Lys | Arg | Gln |
|  |  |  |  | 115 |  |  |  |  | 120 |  |  |  |  | 125 |  |
| CTC | TAC | AGT | GCA | TTG | GCT | AAT | AAA | TGT | TGC | CAT | GTT | GGT | TGT | ACC | AAA | 431
| Leu | Tyr | Ser | Ala | Leu | Ala | Asn | Lys | Cys | Cys | His | Val | Gly | Cys | Thr | Lys |
|  |  | 130 |  |  |  |  | 135 |  |  |  |  | 140 |  |  |  |
| AGA | TCT | CTT | GCT | AGA | TTT | TGC | TGAGATGAAG | CTAATTGTGC | ACATCTCGTA |  |  |  |  |  |  | 482
| Arg | Ser | Leu | Ala | Arg | Phe | Cys |  |  |  |  |  |  |  |  |  |
|  | 145 |  |  |  |  | 150 |  |  |  |  |  |  |  |  |  |

```
TAATATTCAC ACATATTCTT AATGACATTT CACTGATGCT TCTATCAGGT CAATTCTCAT    542
GTTTGACAGC TTATCATCGA TAAGCTTTAA TGCGGTAGTT TATCACAGTT AAATTGCTAA    602
CGCAGTCAGG CACCGTGTAT GAAATCTAAC AATGCGCTCA TCGTCATCCT CGGCACCGTC    662
ACCCTGGATG CTGTAGGCAT AGGCTTGGTT ATGCCGGTAC TGCCGGGCCT CTTGCGGGAT    722
ATCGTCCATT CCGACAGCAT CGCCAGTCAC TATGGCGTGC TGCTAGCGCT ATATGCGTTG    782
ATGCAATTTC TATGCGCACC CGTTCTCGGA GCACTGTCCG ACCGCTTTGG CCGCCGCCCA    842
GTCCTGCTCG CTTCGCTACT TGGAGCCACT ATCGACTACG CGATCATGGC GACCACACCC    902
GTCCTGTGGA TCC                                                      915
```

( 2 ) INFORMATION FOR SEQ ID NO:12:

( i ) SEQUENCE CHARACTERISTICS:
        ( A ) LENGTH: 150 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Gly Arg Glu Leu Val Arg Ala Gln Ile Ala Ile Cys Gly Met Ser Thr
 1               5                   10                  15

Trp Ser Lys Arg Ser Leu Ser Gln Glu Asp Ala Pro Gln Thr Pro Arg
                20                  25                  30

Pro Val Ala Glu Ile Val Pro Ser Phe Ile Asn Lys Asp Thr Glu Thr
             35                  40                  45

Ile Asn Met Met Ser Glu Phe Val Ala Asn Leu Pro Gln Glu Leu Lys
 50                  55                  60

Leu Thr Leu Ser Glu Met Gln Pro Ala Leu Pro Gln Leu Gln Gln His
 65                  70                  75                  80

Val Pro Val Leu Lys Asp Ser Ser Leu Leu Phe Glu Glu Phe Lys Lys
                 85                  90                  95

Leu Ile Arg Asn Arg Gln Ser Glu Ala Ala Asp Ser Ser Pro Ser Glu
                100                 105                 110

Leu Lys Tyr Leu Gly Leu Asp Thr His Ser Arg Lys Lys Arg Gln Leu
            115                 120                 125

Tyr Ser Ala Leu Ala Asn Lys Cys Cys His Val Gly Cys Thr Lys Arg
130                 135                 140

Ser Leu Ala Arg Phe Cys
145                 150
```

( 2 ) INFORMATION FOR SEQ ID NO:13:

( i ) SEQUENCE CHARACTERISTICS:
        ( A ) LENGTH: 593 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
    ( A ) NAME/KEY: CDS
    ( B ) LOCATION: 431..586

( x i ) SEQUENCE DESCRIPTION: SEQ ID NO:13:

```
GAATTCAACT TCTCCATACT TTGGATAAGG AAATACAGAC ATGAAAAATC TCATTGCTGA      60

GTTGTTATTT AAGCTTGCCC AAAAAGAAGA AGAGTCGAAA GAACTGTGTG CGCAGGTAGA     120

AGCTTTGGAG ATTATCGTCA CTGCAATGCT TCGCAATATG GCGCAAAATG ACCAACAGCG     180

GTTGATTGAT CAGGTAGAGG GGGCGCTGTA CGAGGTAAAG CCCGATGCCA GCATTCCTGA     240

CGACGATACG GAGCTGCTGC GCGATTACGT AAAGAAGTTA TTGAAGCATC CTCGTCAGTA     300

AAAAGTTAAT CTTTTCAACA GCTGTCATAA AGTTGTCACG GCCGAGACTT ATAGTCGCTT     360

TGTTTTTATT TTTTAATGTA TTTGTACGCA AGTTCACGTA AAAAGGGTAT CTAGAGGTTG     420

AGGTGATTTT ATG AAA AAG AAT ATC GCA TTT CTT CTT GCA TCT ATG TTC       469
           Met Lys Lys Asn Ile Ala Phe Leu Leu Ala Ser Met Phe
            1               5                  10

GTT TTT TCT ATT GCT ACA AAT GCC TAT GCA GAC TCA TGG ATG GAG GAA       517
Val Phe Ser Ile Ala Thr Asn Ala Tyr Ala Asp Ser Trp Met Glu Glu
         15                  20                  25

GTT ATT AAA TTA TGC GGC CGC GAA TTG GTA CGC GCG CAA ATA GCG ATA       565
Val Ile Lys Leu Cys Gly Arg Glu Leu Val Arg Ala Gln Ile Ala Ile
 30              35                  40                      45

TGC GGT ATG AGT ACA TGG AGT TGAAGAA                                   593
Cys Gly Met Ser Thr Trp Ser
             50
```

( 2 ) INFORMATION FOR SEQ ID NO:14:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Lys Lys Asn Ile Ala Phe Leu Leu Ala Ser Met Phe Val Phe Ser
 1               5                  10                  15

Ile Ala Thr Asn Ala Tyr Ala Asp Ser Trp Met Glu Glu Val Ile Lys
             20                  25                  30

Leu Cys Gly Arg Glu Leu Val Arg Ala Gln Ile Ala Ile Cys Gly Met
         35                  40                  45

Ser Thr Trp Ser
 50
```

( 2 ) INFORMATION FOR SEQ ID NO:15:

( i ) SEQUENCE CHARACTERISTICS:
        ( A ) LENGTH: 1500 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 438..1235

( x i ) SEQUENCE DESCRIPTION: SEQ ID NO:15:

-continued

```
GAATTCAACT TCTCCATACT TTGGATAAGG AAATACAGAC ATGAAAAATC TCATTGCTGA     60

GTTGTTATTT AAGCTTGCCC AAAAAGAAGA AGAGTCGAAA GAACTGTGTG CGCAGGTAGA    120

AGCTTTGGAG ATTATCGTCA CTGCAATGCT TCGCAATATG GCGCAAAATG ACCAACAGCG    180

GTTGATTCAT CAGGTAGAGG GGGCGCTGTA CGAGGTAAAG CCCGATGCCA GCATTCCTGA    240

CGACGATACG GAGCTGCTGC GCGATTACGT AAAGAAGTTA TTGAAGCATC CTCGTCAGTA    300

AAAAGTTAAT CTTTTCAACA GCTGTCATAA AGTTGTCACG GCCGAGACTT ATAGTCGCTT    360

TGTTTTTATT TTTTAATGTA TTTGTAACTA GTACGCAAGT TCACGTAAAA AGGGTATCTA    420

GAGGTTGAGG TGATTTT ATG AAA AAG AAT ATC GCA TTT CTT CTT GCA TCT        470
                   Met Lys Lys Asn Ile Ala Phe Leu Leu Ala Ser
                    1               5                  10
```

| | | | | | | | | | | | | | | | | |
|---|---|---|---|---|---|---|---|---|---|---|---|---|---|---|---|---|
| ATG | TTC | GTT | TTT | TCT | ATT | GCT | ACA | AAT | GCC | TAT | GCA | TCA | GGC | ACT | ACA | 518 |
| Met | Phe | Val | Phe | Ser | Ile | Ala | Thr | Asn | Ala | Tyr | Ala | Ser | Gly | Thr | Thr | |
| | | | 15 | | | | 20 | | | | 25 | | | | | |
| AAT | ACT | GTG | GCA | GCA | TAT | AAT | TTA | ACT | TGG | AAA | TCA | ACT | AAT | TTC | AAG | 566 |
| Asn | Thr | Val | Ala | Ala | Tyr | Asn | Leu | Thr | Trp | Lys | Ser | Thr | Asn | Phe | Lys | |
| | | 30 | | | | 35 | | | | 40 | | | | | | |
| ACA | ATT | TTG | GAG | TGG | GAA | CCC | AAA | CCC | GTC | AAT | CAA | GTC | TAC | ACT | GTT | 614 |
| Thr | Ile | Leu | Glu | Trp | Glu | Pro | Lys | Pro | Val | Asn | Gln | Val | Tyr | Thr | Val | |
| | 45 | | | | 50 | | | | 55 | | | | | | | |
| CAA | ATA | AGC | ACT | AAG | TCA | GGA | GAT | TGG | AAA | AGC | AAA | TGC | TTT | TAC | ACA | 662 |
| Gln | Ile | Ser | Thr | Lys | Ser | Gly | Asp | Trp | Lys | Ser | Lys | Cys | Phe | Tyr | Thr | |
| 60 | | | | 65 | | | | 70 | | | | 75 | | | | |
| ACA | GAC | ACA | GAG | TGT | GAC | CTC | ACC | GAC | GAG | ATT | GTG | AAG | GAT | GTG | AAG | 710 |
| Thr | Asp | Thr | Glu | Cys | Asp | Leu | Thr | Asp | Glu | Ile | Val | Lys | Asp | Val | Lys | |
| | | | 80 | | | | 85 | | | | 90 | | | | | |
| CAG | ACG | TAC | TTG | GCA | CGG | GTC | TTC | TCC | TAC | CCG | GCA | GGG | AAT | GTG | GAG | 758 |
| Gln | Thr | Tyr | Leu | Ala | Arg | Val | Phe | Ser | Tyr | Pro | Ala | Gly | Asn | Val | Glu | |
| | | 95 | | | | 100 | | | | 105 | | | | | | |
| AGC | ACC | GGT | TCT | GCT | GGG | GAG | CCT | CTG | TAT | GAG | AAC | TCC | CCA | GAG | TTC | 806 |
| Ser | Thr | Gly | Ser | Ala | Gly | Glu | Pro | Leu | Tyr | Glu | Asn | Ser | Pro | Glu | Phe | |
| | | 110 | | | | 115 | | | | 120 | | | | | | |
| ACA | CCT | TAC | CTG | GAG | ACA | AAC | CTC | GGA | CAG | CCA | ACA | ATT | CAG | AGT | TTT | 854 |
| Thr | Pro | Tyr | Leu | Glu | Thr | Asn | Leu | Gly | Gln | Pro | Thr | Ile | Gln | Ser | Phe | |
| | 125 | | | | 130 | | | | 135 | | | | | | | |
| GAA | CAG | GTG | GGA | ACA | AAA | GTG | AAT | GTG | ACC | GTA | GAA | GAT | GAA | CGG | ACT | 902 |
| Glu | Gln | Val | Gly | Thr | Lys | Val | Asn | Val | Thr | Val | Glu | Asp | Glu | Arg | Thr | |
| 140 | | | | 145 | | | | 150 | | | | 155 | | | | |
| TTA | GTC | AGA | AGG | AAC | AAC | ACT | TTC | CTA | AGC | CTC | CGG | GAT | GTT | TTT | GGC | 950 |
| Leu | Val | Arg | Arg | Asn | Asn | Thr | Phe | Leu | Ser | Leu | Arg | Asp | Val | Phe | Gly | |
| | | | 160 | | | | 165 | | | | 170 | | | | | |
| AAG | GAC | TTA | ATT | TAT | ACA | CTT | TAT | TAT | TGG | AAA | TCT | TCA | AGT | TCA | GGA | 998 |
| Lys | Asp | Leu | Ile | Tyr | Thr | Leu | Tyr | Tyr | Trp | Lys | Ser | Ser | Ser | Ser | Gly | |
| | | 175 | | | | 180 | | | | 185 | | | | | | |
| AAG | AAA | ACA | GCC | AAA | ACA | AAC | ACT | AAT | GAG | TTT | TTG | ATT | GAT | GTG | GAT | 1046 |
| Lys | Lys | Thr | Ala | Lys | Thr | Asn | Thr | Asn | Glu | Phe | Leu | Ile | Asp | Val | Asp | |
| | | 190 | | | | 195 | | | | 200 | | | | | | |
| AAA | GGA | GAA | AAC | TAC | TGT | TTC | AGT | GTT | CAA | GCA | GTG | ATT | CCC | TCC | CGA | 1094 |
| Lys | Gly | Glu | Asn | Tyr | Cys | Phe | Ser | Val | Gln | Ala | Val | Ile | Pro | Ser | Arg | |
| | 205 | | | | 210 | | | | 215 | | | | | | | |
| ACA | GTT | AAC | CGG | AAG | AGT | ACA | GAC | AGC | CCG | GTA | GAG | TGT | ATG | GGC | CAG | 1142 |
| Thr | Val | Asn | Arg | Lys | Ser | Thr | Asp | Ser | Pro | Val | Glu | Cys | Met | Gly | Gln | |
| 220 | | | | 225 | | | | 230 | | | | | | | 235 | |
| GAG | AAA | GGC | CAA | TTC | AGA | GAA | ATA | TTC | TAC | ATC | ATT | GGA | GCT | GTG | TA | 1190 |
| Glu | Lys | Gly | Gln | Phe | Arg | Glu | Ile | Phe | Tyr | Ile | Ile | Gly | Ala | Val | Val | |
| | | | | 240 | | | | 245 | | | | 250 | | | | |
| TTT | GTG | GTC | ATC | ATC | CTT | GTC | ATC | ATC | CTG | GCT | ATA | TCT | CTA | CAC | | 1235 |
| Phe | Val | Val | Ile | Ile | Leu | Val | Ile | Ile | Leu | Ala | Ile | Ser | Leu | His | | |

|     | 255 | 260 | 265 |     |
|-----|-----|-----|-----|-----|
| TAAAATTCTC | ATGTTTGACA | GCTTATCATC | GATAAGCTTT | AATGCGGTAG TTTATCACAG | 1295 |
| TTAAATTGCT | AACGCAGTCA | GGCACCGTGT | ATGAAATCTA | ACAATGCGCT CATCGTCATC | 1355 |
| CTCGGCACCG | TCACCCTGGA | TGCTGTAGGC | ATAGGCTTGG | TTATGCCGGT ACTGCCGGGC | 1415 |
| CTCTTGCGGG | ATATCGTCCA | TTCCGACAGC | ATCGCCAGTC | ACTATGGCGT GCTCCTAGCG | 1475 |
| CTATATGCGT | TGATGCAATT | TCTAT |     |     | 1500 |

(2) INFORMATION FOR SEQ ID NO:16:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Lys Asn Ile Ala Phe Leu Leu Ala Ser Met Phe Val Phe Ser
 1               5                  10                  15
Ile Ala Thr Asn Ala Tyr Ala Ser Gly Thr Thr Asn Thr Val Ala Ala
                20                  25                  30
Tyr Asn Leu Thr Trp Lys Ser Thr Asn Phe Lys Thr Ile Leu Glu Trp
            35                  40                  45
Glu Pro Lys Pro Val Asn Gln Val Tyr Thr Val Gln Ile Ser Thr Lys
        50                  55                  60
Ser Gly Asp Trp Lys Ser Lys Cys Phe Tyr Thr Thr Asp Thr Glu Cys
65                  70                  75                  80
Asp Leu Thr Asp Glu Ile Val Lys Asp Val Lys Gln Thr Tyr Leu Ala
                85                  90                  95
Arg Val Phe Ser Tyr Pro Ala Gly Asn Val Glu Ser Thr Gly Ser Ala
            100                 105                 110
Gly Glu Pro Leu Tyr Glu Asn Ser Pro Glu Phe Thr Pro Tyr Leu Glu
        115                 120                 125
Thr Asn Leu Gly Gln Pro Thr Ile Gln Ser Phe Glu Gln Val Gly Thr
    130                 135                 140
Lys Val Asn Val Thr Val Glu Asp Glu Arg Thr Leu Val Arg Arg Asn
145                 150                 155                 160
Asn Thr Phe Leu Ser Leu Arg Asp Val Phe Gly Lys Asp Leu Ile Tyr
                165                 170                 175
Thr Leu Tyr Tyr Trp Lys Ser Ser Ser Ser Gly Lys Lys Thr Ala Lys
            180                 185                 190
Thr Asn Thr Asn Glu Phe Leu Ile Asp Val Asp Lys Gly Glu Asn Tyr
        195                 200                 205
Cys Phe Ser Val Gln Ala Val Ile Pro Ser Arg Thr Val Asn Arg Lys
    210                 215                 220
Ser Thr Asp Ser Pro Val Glu Cys Met Gly Gln Glu Lys Gly Gln Phe
225                 230                 235                 240
Arg Glu Ile Phe Tyr Ile Ile Gly Ala Val Val Phe Val Val Ile Ile
                245                 250                 255
Leu Val Ile Ile Leu Ala Ile Ser Leu His
            260                 265
```

(2) INFORMATION FOR SEQ ID NO:17:

(i) SEQUENCE CHARACTERISTICS:
        (A) LENGTH: 301 base pairs ( B ) TYPE: nucleic acid
( C ) STRANDEDNESS: unknown
( D ) TOPOLOGY: unknown ( i i ) MOLECULE TYPE: DNA ( i x ) FEATURE:
( A ) NAME/KEY: CDS
( B ) LOCATION: 7..297

( x i ) SEQUENCE DESCRIPTION: SEQ ID NO:17:

| AAGCTT | ATG | AAA | TCT | AAC | AAT | GCG | CTC | ATC | GTC | ATC | CTC | GGC | ACC | GTC | 48 |
|---|---|---|---|---|---|---|---|---|---|---|---|---|---|---|---|
| | Met | Lys | Ser | Asn | Asn | Ala | Leu | Ile | Val | Ile | Leu | Gly | Thr | Val | |
| | 1 | | | | 5 | | | | | 10 | | | | | |

| ACC | CTG | GAT | GCT | GTA | GGC | ATA | GGC | TTG | GTT | ATG | CCG | GTA | CTG | CCG | GGC | 96 |
|---|---|---|---|---|---|---|---|---|---|---|---|---|---|---|---|---|
| Thr | Leu | Asp | Ala | Val | Gly | Ile | Gly | Leu | Val | Met | Pro | Val | Leu | Pro | Gly | |
| 15 | | | | | 20 | | | | | 25 | | | | | 30 | |

| CTC | TTG | CGG | GAT | ATC | GTC | CAT | TCC | GAC | AGC | ATC | GCC | AGT | CAC | TAT | GGC | 144 |
|---|---|---|---|---|---|---|---|---|---|---|---|---|---|---|---|---|
| Leu | Leu | Arg | Asp | Ile | Val | His | Ser | Asp | Ser | Ile | Ala | Ser | His | Tyr | Gly | |
| | | | 35 | | | | | 40 | | | | | 45 | | | |

| GTG | CTG | CTA | GCG | CTA | TAT | GCG | TTG | ATG | CAA | TTT | CTA | TGC | GCA | CCC | GTT | 192 |
|---|---|---|---|---|---|---|---|---|---|---|---|---|---|---|---|---|
| Val | Leu | Leu | Ala | Leu | Tyr | Ala | Leu | Met | Gln | Phe | Leu | Cys | Ala | Pro | Val | |
| | | | 50 | | | | | 55 | | | | | 60 | | | |

| CTC | GGA | GCA | CTG | TCC | GAC | CGC | TTT | GGC | CGC | CGC | CCA | GTC | CTG | CTC | GCT | 240 |
|---|---|---|---|---|---|---|---|---|---|---|---|---|---|---|---|---|
| Leu | Gly | Ala | Leu | Ser | Asp | Arg | Phe | Gly | Arg | Arg | Pro | Val | Leu | Leu | Ala | |
| | 65 | | | | | 70 | | | | | 75 | | | | | |

| TCG | CTA | CTT | GGA | GCC | ACT | ATC | GAC | TAC | GCG | ATC | ATG | GCG | ACC | ACA | CCC | 288 |
|---|---|---|---|---|---|---|---|---|---|---|---|---|---|---|---|---|
| Ser | Leu | Leu | Gly | Ala | Thr | Ile | Asp | Tyr | Ala | Ile | Met | Ala | Thr | Thr | Pro | |
| | 80 | | | | | 85 | | | | | 90 | | | | | |

| GTC | CTG | TGG | ATCC | 301 |
|---|---|---|---|---|
| Val | Leu | Trp | | |
| 95 | | | | |

( 2 ) INFORMATION FOR SEQ ID NO:18:

( i ) SEQUENCE CHARACTERISTICS:
( A ) LENGTH: 97 amino acids
( B ) TYPE: amino acid
( D ) TOPOLOGY: linear ( i i ) MOLECULE TYPE: protein ( x i ) SEQUENCE DESCRIPTION: SEQ ID NO:18:

| Met | Lys | Ser | Asn | Asn | Ala | Leu | Ile | Val | Ile | Leu | Gly | Thr | Val | Thr | Leu |
|---|---|---|---|---|---|---|---|---|---|---|---|---|---|---|---|
| 1 | | | | 5 | | | | | 10 | | | | | 15 | |

| Asp | Ala | Val | Gly | Ile | Gly | Leu | Val | Met | Pro | Val | Leu | Pro | Gly | Leu | Leu |
|---|---|---|---|---|---|---|---|---|---|---|---|---|---|---|---|
| | | | 20 | | | | | 25 | | | | | 30 | | |

| Arg | Asp | Ile | Val | His | Ser | Asp | Ser | Ile | Ala | Ser | His | Tyr | Gly | Val | Leu |
|---|---|---|---|---|---|---|---|---|---|---|---|---|---|---|---|
| | | 35 | | | | | 40 | | | | | 45 | | | |

| Leu | Ala | Leu | Tyr | Ala | Leu | Met | Gln | Phe | Leu | Cys | Ala | Pro | Val | Leu | Gly |
|---|---|---|---|---|---|---|---|---|---|---|---|---|---|---|---|
| | 50 | | | | | 55 | | | | | 60 | | | | |

| Ala | Leu | Ser | Asp | Arg | Phe | Gly | Arg | Arg | Pro | Val | Leu | Leu | Ala | Ser | Leu |
|---|---|---|---|---|---|---|---|---|---|---|---|---|---|---|---|
| 65 | | | | | 70 | | | | | 75 | | | | | 80 |

| Leu | Gly | Ala | Thr | Ile | Asp | Tyr | Ala | Ile | Met | Ala | Thr | Thr | Pro | Val | Leu |
|---|---|---|---|---|---|---|---|---|---|---|---|---|---|---|---|
| | | | | 85 | | | | | 90 | | | | | 95 | |

Trp ( 2 ) INFORMATION FOR SEQ ID NO:19:

( i ) SEQUENCE CHARACTERISTICS:
( A ) LENGTH: 11 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:19:

Met Lys Lys Asn Ile Ala Phe Leu Leu Arg Lys
1               5                   10

( 2 ) INFORMATION FOR SEQ ID NO:20:

( i ) SEQUENCE CHARACTERISTICS:
      ( A ) LENGTH: 11 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:20:

Met Lys Lys Asn Ile Ala Phe Leu Leu Arg Arg
1               5                   10

( 2 ) INFORMATION FOR SEQ ID NO:21:

( i ) SEQUENCE CHARACTERISTICS:
      ( A ) LENGTH: 11 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:21:

Met Lys Lys Asn Ile Ala Phe Leu Leu Lys Lys
1               5                   10

( 2 ) INFORMATION FOR SEQ ID NO:22:

( i ) SEQUENCE CHARACTERISTICS:
      ( A ) LENGTH: 42 base pairs
      ( B ) TYPE: nucleic acid
      ( C ) STRANDEDNESS: unknown
      ( D ) TOPOLOGY: unknown ( i i ) MOLECULE TYPE: DNA ( x i ) SEQUENCE DESCRIPTION: SEQ ID NO:22:

CTAGAATTAT GAAAAGAAT ATCGCATTTC TTCTTAAACG GG      42

( 2 ) INFORMATION FOR SEQ ID NO:23:

( i ) SEQUENCE CHARACTERISTICS:
      ( A ) LENGTH: 41 base pairs
      ( B ) TYPE: nucleic acid
      ( C ) STRANDEDNESS: unknown
      ( D ) TOPOLOGY: unknown ( i i ) MOLECULE TYPE: DNA ( x i ) SEQUENCE DESCRIPTION: SEQ ID NO:23:

AGTCCCGTTT AAGAAGAAAT GCGATATTCT TTTTCATAAT T      41

( 2 ) INFORMATION FOR SEQ ID NO:24:

( i ) SEQUENCE CHARACTERISTICS:
      ( A ) LENGTH: 42 base pairs
      ( B ) TYPE: nucleic acid
      ( C ) STRANDEDNESS: unknown
      ( D ) TOPOLOGY: unknown ( i i ) MOLECULE TYPE: DNA ( x i ) SEQUENCE DESCRIPTION: SEQ ID NO:24:

CTAGAATTAT GTTCCCAGCT ATGCCTCTAT CTAGTAAACG GG     42

( 2 ) INFORMATION FOR SEQ ID NO:25:

( i ) SEQUENCE CHARACTERISTICS:
        ( A ) LENGTH: 41 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:25:

AGTCCCGTTT ACTAGATAGA GGCATAGCTG GGAACATAAT T     41

( 2 ) INFORMATION FOR SEQ ID NO:26:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:26:

Met Phe Pro Ala Met Pro Leu Ser Ser Lys Arg
1               5                   10

( 2 ) INFORMATION FOR SEQ ID NO:27:

( i ) SEQUENCE CHARACTERISTICS:
        ( A ) LENGTH: 64 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 5..64

( x i ) SEQUENCE DESCRIPTION: SEQ ID NO:27:

CGCG CAG ATT GCC ATT TGC GGC ATG AGC ACC TGG AGC AAA AGG AAA CCC     49
    Gln Ile Ala Ile Cys Gly Met Ser Thr Trp Ser Lys Arg Lys Pro
    1               5                   10                  15

ACT GGT TAT GGT TCT     64
Thr Gly Tyr Gly Ser
                20

( 2 ) INFORMATION FOR SEQ ID NO:28:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

Gln Ile Ala Ile Cys Gly Met Ser Thr Trp Ser Lys Arg Lys Pro Thr
1               5                   10                  15

Gly Tyr Gly Ser
            20

( 2 ) INFORMATION FOR SEQ ID NO:29:

( i ) SEQUENCE CHARACTERISTICS:
        ( A ) LENGTH: 62 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:29:

```
CGAGAACCAT AACCAGTGGG TTTCCTTTTG CTCCAGGTGC TCATGCCGCA AATGGCAATC      60

TG                                                                    62
```

( 2 ) INFORMATION FOR SEQ ID NO:30:

( i ) SEQUENCE CHARACTERISTICS:
        ( A ) LENGTH: 50 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:30:

```
GGCCACTCTG TGCGGTGCTG AACTGGTTGA CGCTCTGCAG TTTGTTTGCG                 50
```

( 2 ) INFORMATION FOR SEQ ID NO:31:

( i ) SEQUENCE CHARACTERISTICS:
        ( A ) LENGTH: 51 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:31:

```
GTCACCGCAA ACAAACTGCA GAGCGTCAAC CAGTTCAGCA CCGCACAGAG T               51
```

( 2 ) INFORMATION FOR SEQ ID NO:32:

( i ) SEQUENCE CHARACTERISTICS:
        ( A ) LENGTH: 55 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:32:

```
GGTCCCGAAA CTCTGTGCGG TGCTGAACTG GTTGACGCTC TGCAGTTTGT TTGCG           55
```

( 2 ) INFORMATION FOR SEQ ID NO:33:

( i ) SEQUENCE CHARACTERISTICS:
        ( A ) LENGTH: 64 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:33:

```
GTCACCGCAA ACAAACTGCA GAGCGTCAAC CAGTTCAGCA CCGCACAGAG TTTCGGGACC      60

TGCA                                                                  64
```

( 2 ) INFORMATION FOR SEQ ID NO:34:

( i ) SEQUENCE CHARACTERISTICS:
  ( A ) LENGTH: 84 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:34:

```
CTAGAATTAT GATGATTACT CTGCGCAAAC TTCCTCTGGC GGTTGCCGTC GCAGCGGGCG    60
TAATGTCTGC TCAGGCCATG GCCA                                          84
```

( 2 ) INFORMATION FOR SEQ ID NO:35:

( i ) SEQUENCE CHARACTERISTICS:
  ( A ) LENGTH: 84 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:35:

```
GATCTGGCCA TGGCCTGAGC AGACATTACG CCCGCTGCGA CGGCAACCGC CAGAGGAAGT    60
TTGCGCAGAG TAATCATCAT AATT                                          84
```

( 2 ) INFORMATION FOR SEQ ID NO:36:

( i ) SEQUENCE CHARACTERISTICS:
  ( A ) LENGTH: 52 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:36:

```
CAACTCTACA GTGCATTGGC TAATAAATGT TGCCATGTTG GTTGTACCAA AA            52
```

( 2 ) INFORMATION FOR SEQ ID NO:37:

( i ) SEQUENCE CHARACTERISTICS:
  ( A ) LENGTH: 60 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:37:

```
GATCTTTTGG TACAACCAAC ATGGCAACAT TTATTAGCCA ATGCACTGTA GAGTTGTGCA    60
```

( 2 ) INFORMATION FOR SEQ ID NO:38:

( i ) SEQUENCE CHARACTERISTICS:
  ( A ) LENGTH: 4 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:38:

```
Lys Arg Lys Pro
 1
```

( 2 ) INFORMATION FOR SEQ ID NO:39:

( i ) SEQUENCE CHARACTERISTICS:
  ( A ) LENGTH: 4 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:39:

Asp Lys Lys Arg
1

( 2 ) INFORMATION FOR SEQ ID NO:40:

( i ) SEQUENCE CHARACTERISTICS:
  ( A ) LENGTH: 4 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:40:

Arg Lys Lys Arg
1

( 2 ) INFORMATION FOR SEQ ID NO:41:

( i ) SEQUENCE CHARACTERISTICS:
  ( A ) LENGTH: 4 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:41:

Arg Arg Arg Lys
1

( 2 ) INFORMATION FOR SEQ ID NO:42:

( i ) SEQUENCE CHARACTERISTICS:
  ( A ) LENGTH: 16 amino acids
  ( B ) TYPE: amino acid
  ( C ) STRANDEDNESS: unknown
  ( D ) TOPOLOGY: unknown ( i i ) MOLECULE TYPE: peptide ( i x ) FEATURE:
  ( A ) NAME/KEY: Xaa
  ( B ) LOCATION: 5
  ( C ) OTHER INFORMATION: Xaa=bond or any amino acid, provided
    that Xaa is compatible with the selective cleavage of
    said non- naturally occurring C-peptide ( i x ) FEATURE:
  ( A ) NAME/KEY: Xaa
  ( B ) LOCATION: 6
  ( C ) OTHER INFORMATION: Xaa=bond or any amino acid, provided
    that Xaa is compatible with the selective cleavage of
    said non- naturally occurring C-peptide ( i x ) FEATURE:
  ( A ) NAME/KEY: Xaa
  ( B ) LOCATION: 7
  ( C ) OTHER INFORMATION: Xaa=bond or any amino acid, provided
    that Xaa is compatible with the selective cleavage of
    said non- naturally occurring C-peptide ( i x ) FEATURE:
  ( A ) NAME/KEY: Xaa (B) LOCATION: 8
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 9
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 10
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 11
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 12
                (C) OTHER INFORMATION: Xaa=bond or any amino acid, provided
                    that Xaa is compatible with the selective cleavage of
                    said non- naturally occurring C-peptide (xi) SEQUENCE DESCRIPTION: SEQ ID NO:42:

Lys Arg Lys Pro Xaa Xaa Xaa Xaa Xaa Xaa Xaa Xaa Arg Lys Lys Arg
1               5                   10                  15

(2) INFORMATION FOR SEQ ID NO:43:

(i) SEQUENCE CHARACTERISTICS:
                (A) LENGTH: 16 amino acids
                (B) TYPE: amino acid
                (C) STRANDEDNESS: unknown
                (D) TOPOLOGY: unknown (ii) MOLECULE TYPE: peptide (ix) FEATURE:
                (A) NAME/KEY: Xaa
                (B) LOCATION: 5
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 6
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 7
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 8
                (C) OTHER INFORMATION: Xaa=bond or any amino acid, provided
                    that Xaa is compatible with the selective cleavage of
                    said non- naturally occurring C-peptide (ix) FEATURE:
                (A) NAME/KEY: Xaa
                (B) LOCATION: 9

( C ) OTHER INFORMATION: Xaa=bond or any amino acid, provided
that Xaa is compatible with the selective cleavage of
said non- naturally occurring C-peptide ( i x ) FEATURE:
 ( A ) NAME/KEY: Xaa
 ( B ) LOCATION: 10
 ( C ) OTHER INFORMATION: Xaa=bond or any amino acid, provided
that Xaa is compatible with the selective cleavage of
said non- naturally occurring C-peptide ( i x ) FEATURE:
 ( A ) NAME/KEY: Xaa
 ( B ) LOCATION: 11
 ( C ) OTHER INFORMATION: Xaa=bond or any amino acid, provided
that Xaa is compatible with the selective cleavage of
said non- naturally occurring C-peptide ( i x ) FEATURE:
 ( A ) NAME/KEY: Xaa
 ( B ) LOCATION: 12
 ( C ) OTHER INFORMATION: Xaa=bond or any amino acid, provided
that Xaa is compatible with the selective cleavage of
said non- naturally occurring C-peptide ( x i ) SEQUENCE DESCRIPTION: SEQ ID NO:43:

```
Asp Lys Lys Arg Xaa Xaa Xaa Xaa Xaa Xaa Xaa Xaa Arg Arg Arg Lys
1               5                       10                      15
```

( 2 ) INFORMATION FOR SEQ ID NO:44:

( i ) SEQUENCE CHARACTERISTICS:
  ( A ) LENGTH: 15 amino acids
  ( B ) TYPE: amino acid
  ( C ) STRANDEDNESS: unknown
  ( D ) TOPOLOGY: unknown ( i i ) MOLECULE TYPE: peptide ( i x ) FEATURE:
  ( A ) NAME/KEY: Xaa
  ( B ) LOCATION: 4
  ( C ) OTHER INFORMATION: Xaa=bond or any amino acid, provided
that Xaa is compatible with the selective cleavage of
said non- naturally occurring C-peptide ( i x ) FEATURE:
  ( A ) NAME/KEY: Xaa
  ( B ) LOCATION: 5
  ( C ) OTHER INFORMATION: Xaa=bond or any amino acid, provided
that Xaa is compatible with the selective cleavage of
said non- naturally occurring C-peptide ( i x ) FEATURE:
  ( A ) NAME/KEY: Xaa
  ( B ) LOCATION: 6
  ( C ) OTHER INFORMATION: Xaa=bond or any amino acid, provided
that Xaa is compatible with the selective cleavage of
said non- naturally occurring C-peptide ( i x ) FEATURE:
  ( A ) NAME/KEY: Xaa
  ( B ) LOCATION: 7
  ( C ) OTHER INFORMATION: Xaa=bond or any amino acid, provided
that Xaa is compatible with the selective cleavage of
said non- naturally occurring C-peptide ( i x ) FEATURE:
  ( A ) NAME/KEY: Xaa
  ( B ) LOCATION: 8
  ( C ) OTHER INFORMATION: Xaa=bond or any amino acid, provided
that Xaa is compatible with the selective cleavage of
said non- naturally occurring C-peptide ( i x ) FEATURE:
  ( A ) NAME/KEY: Xaa
  ( B ) LOCATION: 9

-continued (C) OTHER INFORMATION: Xaa=bond or any amino acid, provided
that Xaa is compatible with the selective cleavage of
said non- naturally occurring C-peptide (ix) FEATURE:
 (A) NAME/KEY: Xaa
 (B) LOCATION: 10
 (C) OTHER INFORMATION: Xaa=bond or any amino acid, provided
  that Xaa is compatible with the selective cleavage of
  said non- naturally occurring C-peptide (ix) FEATURE:
 (A) NAME/KEY: Xaa
 (B) LOCATION: 11
 (C) OTHER INFORMATION: Xaa=bond or any amino acid, provided
  that Xaa is compatible with the selective cleavage of
  said non- naturally occurring C-peptide (xi) SEQUENCE DESCRIPTION: SEQ ID NO:44:

```
Lys Arg Lys Xaa Xaa Xaa Xaa Xaa Xaa Xaa Xaa Arg Arg Arg Lys
 1           5                       10                  15
```

(2) INFORMATION FOR SEQ ID NO:45:

(i) SEQUENCE CHARACTERISTICS:
  (A) LENGTH: 16 amino acids
  (B) TYPE: amino acid
  (C) STRANDEDNESS: unknown
  (D) TOPOLOGY: unknown (ii) MOLECULE TYPE: peptide (ix) FEATURE:
  (A) NAME/KEY: Xaa
  (B) LOCATION: 5
  (C) OTHER INFORMATION: Xaa=bond or any amino acid, provided
   that Xaa is compatible with the selective cleavage of
   said non- naturally occurring C-peptide (ix) FEATURE:
  (A) NAME/KEY: Xaa
  (B) LOCATION: 6
  (C) OTHER INFORMATION: Xaa=bond or any amino acid, provided
   that Xaa is compatible with the selective cleavage of
   said non- naturally occurring C-peptide (ix) FEATURE:
  (A) NAME/KEY: Xaa
  (B) LOCATION: 7
  (C) OTHER INFORMATION: Xaa=bond or any amino acid, provided
   that Xaa is compatible with the selective cleavage of
   said non- naturally occurring C-peptide (ix) FEATURE:
  (A) NAME/KEY: Xaa
  (B) LOCATION: 8
  (C) OTHER INFORMATION: Xaa=bond or any amino acid, provided
   that Xaa is compatible with the selective cleavage of
   said non- naturally occurring C-peptide (ix) FEATURE:
  (A) NAME/KEY: Xaa
  (B) LOCATION: 9
  (C) OTHER INFORMATION: Xaa=bond or any amino acid, provided
   that Xaa is compatible with the selective cleavage of
   said non- naturally occurring C-peptide (ix) FEATURE:
  (A) NAME/KEY: Xaa
  (B) LOCATION: 10
  (C) OTHER INFORMATION: Xaa=bond or any amino acid, provided
   that Xaa is compatible with the selective cleavage of
   said non- naturally occurring C-peptide (ix) FEATURE:
  (A) NAME/KEY: Xaa
  (B) LOCATION: 11
  (C) OTHER INFORMATION: Xaa=bond or any amino acid, provided -continued that Xaa is compatible with the selective cleavage of
said non- naturally occurring C-peptide ( i x ) FEATURE:
( A ) NAME/KEY: Xaa
( B ) LOCATION: 12
( C ) OTHER INFORMATION: Xaa=bond or any amino acid, provided
that Xaa is compatible with the selective cleavage of
said non- naturally occurring C-peptide ( x i ) SEQUENCE DESCRIPTION: SEQ ID NO:45:

Asp Lys Lys Arg Xaa Xaa Xaa Xaa Xaa Xaa Xaa Xaa Arg Lys Lys Arg
1           5                       10                  15

( 2 ) INFORMATION FOR SEQ ID NO:46:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:46:

Thr Gly Tyr Gly Ser
1               5

( 2 ) INFORMATION FOR SEQ ID NO:47:

( i ) SEQUENCE CHARACTERISTICS:
( A ) LENGTH: 6 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:47:

Pro Thr Gly Tyr Gly Ser
1               5

What is claimed is:

1. A process for producing relaxin from a non-naturally occurring prorelaxin wherein said prorelaxin sequentially comprises a leader peptide, a B-chain, a non-naturally occurring C-peptide about 8 to 15 amino acids in length, and an A-chain, said non-naturally occurring prorelaxin having: a first cleavage site comprising the adjacent amino acids of the leader peptide and the B-chain, a second cleavage site comprising the adjacent amino acids of said non-naturally occurring C-peptide and the B-chain, and a third cleavage site comprising the adjacent amino acids of said non-naturally occurring C-peptide and the A-chain, which process comprises:

(a) folding said prorelaxin, (b) contacting said folded prorelaxin with one or more cleaving agent specific for said first second and third cleavage sites, whereby said leader peptide and said non-naturally occurring C-peptide are specifically excised, and (c) recovering the biologically active relaxin so-produced.

2. The process of claim 1 wherein the relaxin is H2 human relaxin.

3. The process of claim 1 wherein one or more of said cleaving agents is one or a combination of enzymes.

4. The process according to claim 3 wherein said enzymes are selected from the group consisting of endoproteinase Asp N, trypsin, endoproteinase Lys C, endoproteinase Arg C and carboxypeptidase B.

5. The process of claim 4 wherein said enzymes are selected from the group consisting of:

trypsin in combination with carboxypeptidase B, endoproteinase Arg C in combination with carboxypeptidase B, endoproteinase Lys C in combination with carboxypeptidase B, or endoproteinase Asp N in combination with endoproteinase Lys C.

6. The process according to claim 4 wherein said enzymes are endoproteinase Lys C in combination with carboxypeptidase B.

7. The process according to claim 4 wherein said enzymes are endoproteinase Asp N in combination with endoproteinase Lys C.

8. The process according to claim 1 wherein said prorelaxin is produced recombinantly by transfecting into appropriate host cells an expression construct containing a nucleic acid encoding prorelaxin, culturing said transfected cells and isolating said prorelaxin from said transfected cells.

9. The process according to claim 8 wherein said prorelaxin isolation includes solubilizing and refolding said prorelaxin.

10. The process of claim 9 wherein said prorelaxin is solubilized with a solution comprising guanidine hydrochloride.

11. The process of claim 9 wherein said prorelaxin is refolded under conditions of dilute protein concentration.

12. The process of claim 9 wherein prorelaxin is refolded using a redox buffer.

13. The process of claim 8 wherein said host cells are *E. coli*.

14. The process of claim 1, wherein said A-chain comprises an N-terminal glutamine, and said process further comprising cyclizing the A-chain N-terminal glutamine.

15. The process of claim 14 wherein the relaxin A-chain N-terminal glutamine is cyclized through a heat step.

16. A process for producing relaxin from a non-naturally occurring prorelaxin wherein said prorelaxin comprises a leader peptide, a B-chain, a non-naturally occurring C-peptide about 8 to 15 amino acids in length, and an A-chain, and wherein said leader peptide comprises a cleavage site adjacent the B-chain and wherein said non-naturally occurring C-peptide comprises cleavage sites adjacent the B-chain and the A-chain and is selected from the group:

Lys Arg Lys Pro Thr Gly Tyr Gly Ser Arg Lys, Lys Arg, (SEQ ID NO:3)

Asp Lys Lys Arg Thr Gly Tyr Gly Arg Arg Arg Lys, (SEQ ID NO:6)

Asp Lys Lys Arg Thr Gly Tyr Gly Ser Arg Lys Lys Arg, (SEQ ID NO:7)

and

Lys Arg Lys Pro Thr Gly Tyr Gly Ser Arg Arg Arg Lys, (SEQ ID NO:8)

which process comprises folding said prorelaxin, removing said leader and said non-naturally occurring C-peptide from said prorelaxin using a cleaving agent at said cleavage sites and recovering relaxin.

17. The process according to claim 1 wherein said leader sequence comprises the amino acid sequence Met Lys Lys Asn Ile Ala Phe Leu Lys Arg. (SEQ ID NO:1)

18. The process according to claim 1 wherein said relaxin is recovered by a process which includes a step selected from the group consisting of adsorption chromatography, ion-exchange chromatography, reverse-phase chromatography, size-exclusion chromatography and ultrafiltration.

19. The process according to claim 1 comprising formulating the relaxin in a formulation buffer.

20. A non-naturally occurring prorelaxin sequentially comprising an optional leader peptide, a B-chain, a non-naturally occurring C-peptide of about 8 to 15 amino acids in length and an A-chain, having:

an optional first cleavage site comprising the adjacent amino acids of the leader peptide and the B-chain, a second cleavage site comprising the adjacent amino acids of said non-naturally occurring C-peptide and the B-chain, and a third cleavage site comprising the adjacent amino acids of said non-naturally occurring C-peptide and the A-chain;

said optional leader peptide and said non-naturally occurring C-peptide being selectively cleaveable at said cleavage sites, and said B- and A-chains having the disulfide bridges of naturally occurring relaxin.

21. A prorelaxin comprising a leader peptide, a B-chain, a non-naturally occurring C-peptide about 8 to 15 amino acids in length, and an A-chain, wherein said leader peptide comprises a cleavage site adjacent the B-chain and wherein said non-naturally occurring C-peptide comprises cleavage sites adjacent the B-chain and the A-chain and is selected from the group;

Lys Arg Lys Pro Thr Gly Tyr Gly Ser Arg Lys Lys Arg, (SEQ ID NO:3)

Asp Lys Lys Arg Thr Gly Tyr Gly Arg Arg Arg Lys, (SEQ ID NO:6)

Asp Lys Lys Arg Thr Gly Tyr Gly Ser Arg Lys Lys Arg, (SEQ ID NO:7)

and

Lys Arg Lys Pro Thr Gly Tyr Gly Arg Arg Arg Lys. (SEQ ID NO:8)

22. The prorelaxin according to claim 20 wherein said leader sequence comprises the amino acid sequence Met Lys Lys Asn Ile Ala Phe Leu Leu Lys Arg. (SEQ ID NO:1)

23. An isolated DNA encoding the prorelaxin of claim 20.

24. An expression vector operatively containing the DNA encoding the prorelaxin of claim 20.

25. A host cell transfected with the vector of claim 24.

26. A relaxin composition produced by (a) folding a non-naturally occurring prorelaxin, said prorelaxin sequentially having an optional leader peptide, a B-chain, a non-naturally occurring C-peptide about 8 to 15 amino acids in length, and an A-chain, including an optional first cleavage site comprising the adjacent amino acids of the leader peptide and the B-chain, a second cleavage site comprising the adjacent amino aids of said non-naturally occurring C-peptide and the B-chain, and a third cleavage site comprising the adjacent amino acids of said non-naturally occurring C-peptide and the A-chain: (b) contacting the folded prorelaxin with one or more cleaving agents specific for said second and third cleavage sites and optionally said first cleavage site, whereby said leader peptide and said non-naturally occurring C-peptide are specifically excised, and (c) recovering the biologically active relaxin so-produced; said composition comprising: said B-chain and said A-chain connected by the disulfide bridges of naturally occurring relaxin, and said excised non-naturally occurring C-peptide or an enzymatically cleaved fragment thereof.

27. The process of claim 1 wherein the amino acid sequence of said second cleavage site on said non-naturally occurring C-peptide is selected from the group:

Lys Arg Lys Pro, (SEQ ID NO:38)

Asp Lys Lys Arg, (SEQ ID NO:39)

and

Lys Arg Lys.

28. The process of claim 27 wherein the amino acid sequence of said third cleavage site on said non-naturally occurring C-peptide is selected from the group:

Arg Lys Lys Arg (SEQ ID NO:40)

and

Arg Arg Arg Lys. (SEQ ID NO:41)

29. The process of claim 1 wherein the amino acid sequence of said third cleavage site on said non-naturally occurring C-peptide is selected from the group:

Arg Lys Lys Arg                            (SEQ ID NO:40)

and

Arg Arg Arg Lys.                            (SEQ ID NO:41)

30. The process of claim 1 wherein the amino acid sequence of said non-naturally occurring C-peptide is selected from the group:

Lys Arg Lys Pro Xaa Arg Lys Lys Arg,        (SEQ ID NO:42)

Asp Lys Lys Arg Xaa Arg Arg Arg Lys,        (SEQ ID NO:43)

Lys Arg Lys Xaa Arg Arg Arg Lys,            (SEQ ID NO:44)

and

Asp Lys Lys Arg Xaa Arg Lys Lys Arg,        (SEQ ID NO:45)

wherein Xaa is bond or any polypeptide sequence of from 1 to 8 amino acids, provided that the Xaa sequence is compatible with the selective cleavage of said non-naturally occurring C-peptide.

31. The process of claim 30 wherein Xaa is selected from the group:

Thr Gly Tyr Gly Ser                         (SEQ ID NO:46)

and

Pro Thr Gly Tyr Gly Ser.                    (SEQ ID NO:47)

32. The relaxin of claim 26 wherein said non-naturally occurring C-peptide is selected from the group:

(SEQ ID NO:3)
Lys Arg Lys Pro Thr Gly Tyr Gly Ser Arg Lys Lys Arg, (SEQ ID NO:6)
Asp Lys Lys Arg Thr Gly Tyr Gly Arg Arg Arg Lys, (SEQ ID NO:7)
Asp Lys Lys Arg Thr Gly Tyr Gly Ser Arg Lys Lys Arg, and (SEQ ID NO:8)
Lys Arg Lys Pro Thr Gly Tyr Gly Ser Arg Arg Arg Lys.

33. The non-naturally occurring prorelaxin of claim 20 wherein the amino acid sequence of said second cleavage site on said non-naturally occurring C-peptide is selected from the group:

Lys Arg Lys Pro,                              (SEQ ID NO:38)

Asp Lys Lys Arg,                             (SEQ ID NO:39)

and

Lys Arg Lys.

34. The non-naturally occurring prorelaxin of claim 33 wherein the amino acid sequence of said third cleavage site on said non-naturally occurring C-peptide is selected from the group:

Arg Lys Lys Arg                            (SEQ ID NO:40)

and

Arg Arg Arg Lys.                            (SEQ ID NO:41)

35. The non-naturally occurring prorelaxin of claim 20 wherein the amino acid sequence of said third cleavage site on said non-naturally occurring C-peptide is selected from the group:

Arg Lys Lys Arg                            (SEQ ID NO:40)

and

Arg Arg Arg Lys.                            (SEQ ID NO:41)

36. The non-naturally occurring prorelaxin of claim 20 wherein the amino acid sequence of said non-naturally occurring C-peptide is selected from the group:

Lys Arg Lys Pro Xaa Arg Lys Lys Arg        (SEQ ID NO:42),

Asp Lys Lys Arg Xaa Arg Arg Arg Lys        (SEQ ID NO:43),

Lys Arg Lys Xaa Arg Arg Arg Lys            (SEQ ID NO:44), and

Asp Lys Lys Arg Xaa Arg Lys Lys Arg        (SEQ ID NO:45), wherein Xaa is bond or any polypeptide sequence of from 1 to 8 amino acids, provided that the Xaa sequence is compatible with selective cleavage of said non-naturally occurring C-peptide.

37. The non-naturally occurring prorelaxin of claim 36 wherein Xaa is selected from the group:

Thr Gly Tyr Gly Ser                         (SEQ ID NO:46)

and

Pro Thr Gly Tyr Gly Ser.                    (SEQ ID NO:47)

* * * * *